United States Patent [19]

Schiestl

[11] Patent Number: 4,997,757
[45] Date of Patent: Mar. 5, 1991

[54] PROCESS FOR DETECTING POTENTIAL CARCINOGENS

[75] Inventor: Robert H. Schiestl, Rochester, N.Y.
[73] Assignee: GeneBioMed, Inc., Rochester, N.Y.
[21] Appl. No.: 193,345
[22] Filed: May 12, 1988

Related U.S. Application Data

[63] Continuation-in-part of Ser. No. 137,325, Dec. 23, 1987, abandoned.
[51] Int. Cl.$^5$ .................. C12N 15/00; C12Q 1/02; C12Q 1/68
[52] U.S. Cl. .................. 435/172.1; 435/29; 435/6; 435/172.3; 935/76; 935/78; 935/79; 935/84
[58] Field of Search .................. 435/6, 29, 91, 172.1, 435/172.3, 255, 256, 320; 935/76, 78, 79, 84

[56] References Cited

U.S. PATENT DOCUMENTS

| | | | |
|---|---|---|---|
| 4,256,832 | 3/1981 | Findl et al. | 435/6 |
| 4,469,786 | 9/1984 | Garro et al. | 435/7 |
| 4,701,406 | 10/1987 | Chou | 435/5 |

OTHER PUBLICATIONS

Scherer et al., Proc Natl Acad Sci., vol. 76, pp. 4951–4955, "Replacement of Chromosome Segments with Altered DNA Sequence Constructed in vitro" 1979.

"Methods for Detecting Carcinogens and Mutagens with the Salmonella/Mammalian Microsome Mutagenicity Test" Bruce N. Ames, Joyce McCann & Edith Yamasaki (Mutation Research, Amsterdam, 1973), pp. 347–363.

"Detection of Carcinogens as Mutagens in the Salmonella/Microsome Test: Assay of 300 Chemicals" Joyce McCann et al. (Proc. National Academy of Science, vol. 72, No. 12, Dec. 1975), pp. 5135–5139.

"Gene Conversion Between Duplicated Genetic Elements in Yeast" Jennifer A. Jackson & Gerald R. Fink (Nature, vol. 292, Jul. 1981), pp. 306–311.

"X-Ray Enhances Mating Type Switching in Heterothallic Strains of Saccharomyces cerevisiae" Robert Schiestl and Ulrike Wintersberger (Mol Gen Genet 196–1982), pp. 512–517.

"Induction of Mating Type Interconversion in a Heterothallic Strain of Saccharomyces cerevisiae by DNA Damaging Agents" Robert Schiestl and Ulrike Wintersberger (Mol Gen Genet 191–1983), pp. 59–65.

"Testing of Chemicals for Genetic Activity with Saccharomyces cerevisiae: A Report of the U.S. Environmental Protection Agency Gene-Tox Program", (Mutation Research, 133–1984), pp. 199–244.

(List continued on next page.)

Primary Examiner—Robin L. Teskin
Attorney, Agent, or Firm—Howard J. Greenwald

[57] ABSTRACT

There is provided a process for screening an agent in order to determine whether such agent increases the frequency of genome rearrangement in living matter.

In the first step of this process, there is provided a viable species of Saccharomyces cerevisiae yeast which comprises repeated genetic elements in its haploid genome. These repeated genetic elements are selected from the group consisting of functional and non-functional genetic elements; and these elements are sufficiently homologous so that, under ambient conditions, they recombine with each other and give rise to an indentifiable genome rearrangement which is a deletion.

In the second step of this process, the viable species of yeast is exposed to the agent to be tested. Thereafter, it is plated onto a growth medium which, after the exposed yeast species grows upon it, facilitates the identification of those yeast which have undergone said genome rearrangement.

In the last step of the process, the extent to which the exposed species of yeast has undergone genome rearrangement is determined.

Also disclosed is a the viable yeast strain used in said process, the plasmid used to construct said strain, and a process for constructing said strain.

20 Claims, 7 Drawing Sheets

OTHER PUBLICATIONS (*Communications in Molecular Biology, Mechanisms of Yeast Recombination* Edited by Amal Klal and Jeffrey Strathern, Cold Spring Harbor, New York 1986), pp. 85–88.

"A Method of Gene Disruption that Allows Repeated Use of UR3 Selection in the Construction of Multiply Disrupted Yeast Strains" Eric Alani et al., (*Genetics*, the Genetics Society of America, Aug. 1987), pp. 541–545.

"Recombinational Substrates Designed to Study Recombination Between Unique and Repetitive Sequences in vivo" Michael T. Fasullo and Ronald W. Davis (Proceedings of the National Academy of Sciences, vol. 84, Sep. 1987), pp. 6215–6219.

PROCESS FOR DETECTING POTENTIAL CARCINOGENS

CROSS-REFERENCE TO RELATED APPLICATION

This application is a continuation-in-part of applicant's copending application U.S. Ser. No. 137,325, filed Dec. 23, 1987, now abandoned.

FIELD OF THE INVENTION

A process for predicting the carcinogenic potential of a compound or composition using the yeast Saccharomyces cerevisiae wherein the yeast is incubated in the presence of the compound or composition.

BACKGROUND OF THE INVENTION

About 700,000 new cases of cancer affect North Americans each year. It is estimated that from about 70 to about 90 percent of these new cancer cases are linked to environmental carcinogens. Epidemiologists estimate that at least about 70 percent of human cancer would be preventable if the main risk and antirisk factors could be identified. One epidemiological example of this phenomenon is colon and breast cancer. These are among the major types of cancer, but they are quite rare among Japanese living in Japan. However, Japanese living in the United States have a relatively high incidence of this disease.

There are in excess of about 80,000 chemicals in commercial production. Over 400,000 new organic compounds are synthesized every year, and at least 1,000 of them each year will eventually be introduced into economic use. There is a need to be able to determine which of these new compounds will cause cancer. However it is often difficult to predict without testing whether any particular chemical will cause cancer.

The most reliable means for determining whether a particular compound is carcinogenic is a long term assay, which generally is based on the experimental assessment of the potential of the substance to induce tumors in rodents. Long term assays usually take from 6 to 12 months to conduct, and they are relatively expensive. Because of the time and/or the expense involved, it is not feasible to conduct long term assays in many situations, especially where one is seeking a preliminary indication as to whether to proceed with the development of a particular substance.

The need for relatively fast and inexpensive means for preliminarily evaluating the cancer-causing potential of new chemicals has led to the development of many short term assays; some of these short term assays are described in column 4 (lines 13-44) of U.S. Pat. No. 4,701,406, the disclosure of which is hereby incorporated by reference into this specification. The most widely known of these short-term assays is the Ames Assay. This Assay is based upon the assumption that carcinogens will cause the genetic reversion of certain mutant strains of bacteria such as Salmonella typhimurium. In other words, the mutant strains revert to their normal form in the presence of mutagens. A description of the Ames Assay may be found, e.g., in an article by Ames et al., "Methods for Detecting Carcinogens and Mutagens with the Salmonella/Mammalian-Microsome Mutagenicity Test," Mutation Research, vol. 31 (1975), pp. 347-364.

One disadvantage of the Ames Assay is that is cannot evaluate compounds which are bactericidal. Yet another disadvantage of the Ames Assay is that many classes of carcinogenic compounds consistently show poor responses in this Assay and also in mammalian cell genotoxic assay systems. Thus, as is disclosed at column 4 of U.S. Pat. No. 4,701,406, the Ames Assay is not very useful for evaluating certain metals, steroid hormones, and chlorinated hydrocarbons which, although they are known to be carcinogens, give very poor responses.

One of the major problems with the Ames Assay is that, although it is useful for evaluating certain mutagenic compounds, it is not generally useful for evaluating carcinogenic compounds which are not mutagenic. See, for example, McCann et al., "Detection of Carcinogens as Mutagens in the Salmonella/Microsome Test: Assay of 300 Chemicals, Proc. Nat. Acad. Sci. USA, vol. 72, No. 129 (1975), pp. 5135-5139. Also see McCann et al., "Detection of Carcinogens as Mutagens in the Salmonella/Microsome Test: Assay of 300 Chemicals Discussion, "Proc. Nat. Acad. Sci. USA, vol. 73, No. 3 (1976), pp 950-954.

Short term assays involving mutation and recombination assays with the yeast Saccharomyces cerevisiae have been developed. However, these yeast assays are only able to detect about 74 percent of the known carcinogens as being positive. See, for example, an article by Zimmermann et al. appearing in Mutation Research, vol. 133 at pages 199-244 (1984).

The prior art teaches the use of both the Ames Assay and the aforementioned yeast assay in combination, but even the use of both of these assays fails detect many nonmutagenic carcinogens. See, e.g., the aforementioned article by Zimmermann et al.

Not only do the prior art short-term tests fail to show positive results with many known carcinogens, but they also usually fail to indicate whether a prospective carcinogen will cause genome rearrangement. There is a substantial body of literature indicating that compounds which cause genome rearrangement might cause cancer. Thus, it has been shown that the excision of retroviruses from genomes can cause cancer, see Bishop, Ann. Rev. Biochem. 52:301-354 (1983) and Bishop, Cell 42:23-38 (1985). Thus, it has been shown that amplification of specific human DNA sequences up to 120 times are associated with cancer, see Montgomery et al., Proc. Natl. Acad. Sci. USA 80:5724-5728 (1983) and Schwab et al., Proc. Natl. Acad. Sci. USA 81:4940-4944. Thus, it has been shown that immunoglobulin class switching in B lymphocyte differentiation is associated with cancer; see Brown et al., Proc. Natl. Acad. Sci. USA 82:556-560 (1985), Korsmeyer et al., Proc. Natl. Acad. Sci. USA 80:4522-4526 (1983), and Cleary et al., Proc. Natl. Acad. Sci. USA 81:593-597 (1984). Thus it has also been shown that rearrangements involving the T Cell receptor gene are associated with cancer; see Flug, Proc. Natl. Acad. Sci. USA 82:3460-3464 (1985) and Minden et al. Proc. Natl. Acad. Sci. USA 82:1224-1227 (1985). Thus, it has also been shown that amplification preceded by mutation of a gene is associated with cancer; see, e.g., Fujita, Proc. Natl. Acad. Sci. USA 82:3849-3853 (1985). The role of genome rearrangement in carcinogenesis has also been discussed in more general terms in Klein, Nature 294:313-318 (1981), Pall, Proc. Natl. Acad. Sci. USA 78:2465-2468 (1981), Cairns, Nature 289:353-357 (1981), and Wintersberger, Naturwissenschaften 69:107-113 (1982).

It is an object of this invention to provide a short-term assay system which can be used to evaluate many bactericidal compounds.

It is another object of this invention to provide a short-term assay which can be used to evaluate many non-mutagenic compounds which are carcinogenic and which do not show positive results in the prior art Ames Assay and yeast assay system.

It is yet another abject of this invention to provide a short-term assay system which can be used to evaluate many compounds or compositions which cause genome rearrangement.

SUMMARY OF THE INVENTION

In accordance with this invention, there is provided a process for screening an agent in order to determine whether such agent increases the frequency of genome rearrangement in living matter.

In the first step of this process, there is provided a viable species of Saccharomyces cerevisiae yeast which comprises repeated genetic elements in its haploid genome. These repeated genetic elements are selected from the group consisting of functional and nonfunctional genetic elements; and these elements are sufficiently homologous so that, under ambient conditions, they recombine with each other and give rise to an identifiable genome rearrangement which is a deletion.

In the second step of this process, the viable species of yeast is exposed to the agent to be tested. Thereafter, it is plated onto a growth medium which, after the exposed yeast species grows upon it, facilitates the identification of those yeast which have undergone said genome rearrangement.

In the last step of the process, the extent to which the exposed species of yeast has undergone genome rearrangement is determined.

Also disclosed is the viable yeast strain used in said process, the plasmid used to construct said strain, and a process for constructing said strain.

DESCRIPTION OF THE DRAWINGS

The present invention will be more fully understood by reference to the following detailed description thereof, when read in conjuction with the attached drawings, wherein like reference numerals refer to like elements, and wherein:

FIG. 1 is a schematic of the constituents of a preferred embodiment showing recombination between the repeated elements giving rise to a genome rearrangement which is a deletion and the reversion of a disrupted gene is selectable for;

FIG. 3 is a schematic of the constituents of another preferred embodiment showing recombination between the repeated elements giving rise to a genome rearrangement which is a gene duplication and reconstitution of a selectable gene from different parts of it is selected for;

FIG. 4 is a schematic of the constituents of yet another preferred embodiment showing recombination between the repeated elements giving rise to a genome rearrangement which is a translocation and reconstitution of a selectable gene from different parts of it on different chromosomes is selectable for;

FIG. 5 is a schematic of the constituents of yet another preferred embodiment showing recombination between the repeated elements giving rise to a genome rearrangement which is intrachromosomal gene conversion and expression of the new allele in new position gives rise to change of the phenotype which is selectable for;

DESCRIPTION OF THE PREFERRED EMBODIMENTS

Figure 1:
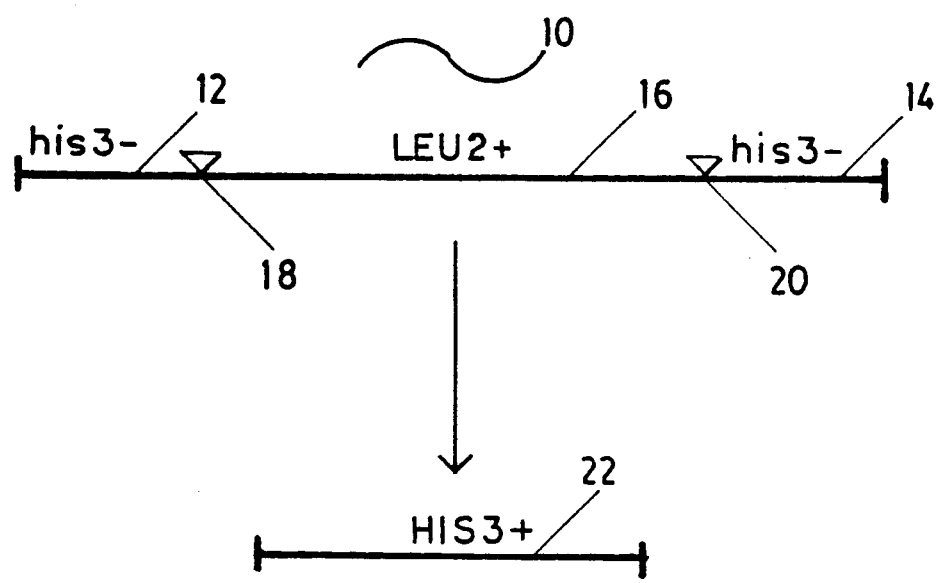

The present invention provides a short term assay for identifying potential carcinogens. This system screens for a genetic endpoint, namely genome rearrangement, which is frequently associated with cancer.

As used in this specification, the term genetic endpoint refers to the secondary effect of genotoxic substances. Genotoxic substances interact with DNA and thereby change its structure. These substances either can bind to the DNA, can modify one or more bases in the DNA strands, can form adducts with one or more of the bases on the bases, can alkylate the DNA, can induce single or double strand breaks, can induce bases adjacent to each other on one DNA strand to pair with each other instead of with the complementary bases on the opposite DNA strand, can intercalate between the stacked bases of the DNA double helix, can cause the DNA strands to bind to each other by other than hydrogen bonds, and the like. These adverse interactions, which are often referred to as lesions, are discussed in U. Goodenough's "Genetics," Third Edition (Saunders College Publishing, New York, 1984), the disclosure of which is hereby incorporated by reference into this specification.

DNA repair enzymes recognize the damage caused by genotoxic substances or by other causes (such as spontaneous damage or misreplication) and repair such damage. In the process of repairing the damage, the native DNA sequence of bases is changed. Wherever a change in the DNA sequence has been caused by both the damage and the subsequent repair, a genetic endpoint exists.

By way of illustration and not limitation, a mutation is a genetic endpoint. As used in this specification, the term mutation refers to a change in a single base pair or in several base pairs. Thus, for example, if one of the bases in a base pair is changed, a lesion occurs, but this is not a mutation within the meaning of this specification; only when both of the complementary base pairs change does a mutation occur. The term mutation, as used in this specification, is equivalent to the term "point mutation" as that term is defined on page 202 of the aforementioned Goodenough book.

The base pair may be changed by several mechanisms. One base pair may be changed to another one. Certain chemicals change the chemical identity of one of the bases, the DNA repair or replication enzymes might misread the damaged base, and the enzymes then might modify the heretofore unchanged base.

By way of illustration and not limitation, crossing over is a genetic endpoint. Crossing over is reciprocal recombination joining different homologous DNA molecules so that genes combined as A-Band a-b are now arranged A-b and a-B. Crossing over might result from the breaking and reunion between two homologous chromosomes. Homologs are chromosomes that are sufficiently similar to pair during meiosis.

By way of illustration and not limitation, gene conversion is a genetic endpoint. As used in this specification, gene conversion is the nonreciprocal transfer of information in terms of DNA sequence from one DNA double strand to another so that, for example, genes ABC and abc are converted to AbC and abc. Gene conversion is discussed on pages 561-565 of the aforementioned Goodenough book.

By way of illustration and not limitation, recombination is a genetic endpoint. Recombination includes both crossing over and gene conversion. Homology between the recombining alleles usually has to exist before recombination occurs.

Genome rearrangement is another genetic endpoint, the one for which the system of this invention tests. A genome is a complete haploid set of chromosomes. A haploid is a viable structure (organism) having a single set of chromosomes; by comparison, a diploid has two sets of chromosomes. A genome rearrangement is any genetic event which rearranges the order of genes in a haploid genome, thereby creating a new environment for particular genes either on a different chromosome or on the same chromosome in a different position. Genome rearrangements include, e.g., deletions, translocations, gene amplification, and rearrangements within genes.

Deletions identify a loss of any DNA sequence from the genome. A translocation involves the interchange of position of segments of nonhomologous chromosomes. Gene amplification is a multiplication of a DNA sequence whereby, e.g., a gene sequence is duplicated, triplicated, etc. Intrachromosomal recombination is recombination within one chromosome, either intrachromatid (within one chromatid) or between sister chromatids. As is known by those skilled in the art, the term chromatid refers to the two parts of a chromosome which exist after replication, there being one DNA double helix before replication, and two identical DNA double helices the basis element of a chromatid, attached at the centromere of a replicated chromosome; intrachromosomal recombination often causes a genetic endpoint. Interchromosomal recombination is recombination between homologous chromosomes in a diploid, and it also often causes a genetic endpoint.

Chapters 7, 17, and 19 of the aforementioned Goodenough book discuss genetic endpoints. Many of the terms used in this specification are defined in the Goodenough book and also in a text by W. Ralph Singleton entitled "Elementary Genetics", Second Edition (American Book Company, N. Y., 1962), at pages 537-559, the disclosure of which is hereby incorporated by reference into this specification.

In the process of this invention, a genus of the yeast *Saccharomyces cerevisiae* with certain specified properties are used in conjunction with a specified medium to test for the presence of chemicals causing genome rearrangement. The yeast used in this process must undergo recombination between repeated genetic elements and thereby cause genome rearrangement which must be selectable for or otherwise identifiable.

The yeast *Saccharomyces cerevisiae* has been extensively used in the field of classical genetics. Because of its properties, it is extremely useful in molecular biology research. These properties include an extremely high frequency of homologous recombination, which allows one to readily make specific constructions in the genome. Thus, for example, one can readily reintroduce certain in vitro constructed altered genes into its genomic position.

Not every species of said yeast works in the process of this invention. The process utilizes those viable species of *Saccharomyces cerevisiae* which contains repeated genetic elements (alleles) in its haploid genome.

The term "viable", as used in connection with alleles, refers to the presence of a least two homologous elements in the haploid genome. Thus, by way of illustration, yeast chromosomes normally only contain one HIS3 gene. In order to be used in the process of this invention, the yeast chromosomes should contain at least two HIS3 (or other) genes in the haploid genome.

By way of illustration and not limitation, one of class of homologous elements which can be used is two alleles of one gene. The alleles may be either functional or nonfunctional. When nonfunctional alleles are used, they may interact by recombination with each other, thereby giving rise to at least one functional allele which can be selected for. When two functional or nonfunctional alleles are used, they may also interact by recombination with each other; by way of illustration, two functional or nonfunctional alleles may recombine with each other to delete the region between the two alleles which can be selected against. In either case, the homologous alleles recombine to create a genome rearrangement. It should also be noted that, regardless of which homologous elements are used, they must recombine to give rise to a genome rearrangement.

Thus, by way of illustration, one class of homologous elements which can be used includes at least two alleles, at least one of which is nonfunctional, and at least one of which is functional. The functionality or non-functionality of these alleles depends upon their genomic position, which determines whether they are expressed.

FIG. 1 illustrates one class of homologous elements which can be present in the yeast used in applicant's process. Referring to FIG. 1, construct 10 is comprised of his3—allele 12, the homologous his3—allele 14, and the LEU2 gene 16. Points 18 and 20 indicate where deletions have been constructed in vitro from the parent HIS3 gene. Because of the deletions constructed at points 18 and 20, alleles 12 and 14 are nonfunctional; however, when they recombine, they form a functional HIS3+ gene.

The construct of FIG. 1 is only one of many within the scope of this invention which can utilize at least two nonfunctional alleles. Thus, by way of illustration and not limitation, alleles 12 and 14 may be trp1—, leu2—, ura3—, lys2—, and the like. Thus, by way of illustration and not limitation, the LEU2 16 gene may be replaced by HIS3, TRP1, URA3, LYS2, and the like.

In the construct of FIG. 1, an auxotrophic marker must be present. As used in this specification, an auxotrophic marker is a mutation which causes the strain to require growth factor(s) which are not required by the wild type. Thus, referring to FIG. 1, construct 10 contains two nonfunctional his3−alleles which cause the strain to require histidine in the medium in order to grow. If one were to substitute lys2− for the his3−alleles, the strain would require lysine to grow.

Referring again to FIG. 1, gene 16 should be a wild type allele, i.e., when the system used in applicant's invention is constructed, gene 16 is selected for to give rise to construct 10. In this process, a wild type allele is disrupted. By way of illustration, as shown in FIG. 1, the HIS3 gene is disrupted. This selection process will be illustrated later in this specification and can be carried out with any other selectable wild type gene such as TRP1, URA3, LYS2, and HIS3 or the like.

Construct 10 spontaneously reverts to its respective wild type gene 22 under ambient conditions. Thus, for example, the yeast strain which contains construct 10 illustrated in FIG. 1 reverts to the HIS3+ wild type gene 22 at a frequency of $3.6 \times 10^{-4}$ occurrences per cell. This yeast strain, designated "RSY6", was deposited on Nov. 30, 1987 with the American Type Culture Collection of 12301 Parklawn Drive, Rockville, Md. as number 20871 by GeneBioMed, Inc. of Rochester, N.Y. One of the unique advantages of construct 10 is that, when the strain containing construct 10 is growing in the presence of a nonmutagenic carcinogen, the rate of reversion to its wild type gene 22 increases substantially.

As those skilled in the art are aware, one can measure the rate of reversion of his− to HIS+ by means well known to those skilled in the art. Thus, for example, one can plate certain numbers of cells on a medium lacking histidine. This and other yeast genetics methods are described in detail in a publication by F. Sherman et al. entitled "Methods in yeast genetics, a laboratory manual" (Cold Spring Harbor Laboratory, Cold Spring Harbor, N.Y., 1986), the entire disclosure of which is hereby incorporated by reference into this specification.

In one of the preferred embodiments of this invention, illustrated in FIG. 1, the viable species of *Saccharomyces cerevisiae* yeast contains repeated genetic elements which recombine to give rise to an identifiable deletion at a rate of at least about $1 \times 10^{-9}$ occurrences per cell per generation, as measured in accordance with the procedure described in the Sherman et al. reference.

As used in this specification, the term "identifiable" refers to a rearrangement which, when the cells in which it is present are growing in a suitable selection medium, cause the cells to exhibit some phenotype which is different from that of cells which have not undergone rearrangement. Thus, by way of illustration, if the genome rearrangement causes the cells to form countable and/or visible colonies, the rearrangement is identifiable if cells which have not undergone the rearrangement do not form countable and/or visible colonies in the selection medium. Thus, by way of illustration, if the genome rearrangement causes the cells to form colonies identifiable by different color from the colonies which have not undergone the rearrangement, the rearrangement is identifiable. Thus, by way of illustration and not limitation, if the genome rearrangement causes the cells to grow, the growth of these cells in selection medium can be measured by the technique described in U.S. Pat. No. 4,256,832 of Findl et al. (which technique detects oxygen consumption of growing cultures), and this growth is thus identifiable.

It is preferred that the repeated genetic elements of the yeast recombine to form identifiable deletions at a rate of at least about $1 \times 10^{-7}$ occurrences per cell per generation. In another embodiment, the repeated genetic elements of the yeast recombine to form identifiable deletions at a rate of at least about $1 \times 10^{-4}$ occurrences per cell per generation.

Thus, referring again to FIG. 1, if construct 10, in the presence of the medium to be discussed later on, reverts to gene 22 in the presence of a chemical at a rate substantially higher than $3.6 \times 10^{-4}$ occurrences per cell per generation, then the chemical induces the recombination mechanism tested for.

Figure 2:
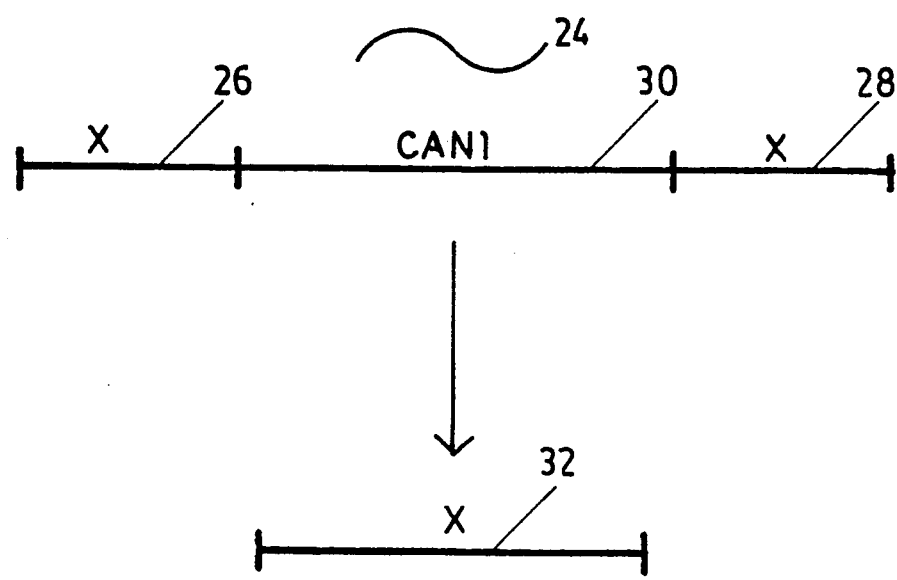
FIG. 2 is a schematic of the constituents of a preferred embodiment showing recombination between the repeated elements giving rise to a genome rearrangement which is a deletion and the presence of the gene to be deleted by said genome rearrangement is selected against.

In the embodiment illustrated in FIG. 2, a construct 24 which contains two homologous genetic elements 26 and 28 are shown. Genetic elements 26 and 28 can be—but need not be—alleles or genes; any genetic elements which have sufficient homology with each other to recombine can be used as elements 26 and 28. Thus, by way of illustration and not limitation, one can use any of the aforementioned mutant or wild type alleles, any DNA sequence which has enough homology to recombine, any cloned gene and the like.

Referring again to FIG. 2, the recombination occurs and deletes the wild type allele 30. Wild type allele 30 must be capable of being selected against so that elements 26 and 28 can recombine to form a structure which contains only one copy of the combination of elements 26 and 28 which contains all or part of the genetic information of element 26 and/or all or part of the genetic information of element 28.

By way of illustration, wild type allele 30 can be the CAN1 gene. When this CAN1 gene is present in construct 24, the strain containing this construct is unable to grow in a medium containing canavanine. Under ambient conditions, alleles 26 and 28 recombine with each other to form a deletion of the CAN1 gene, thereby producing allele 32. After recombination, however, the strain containing allele 32 is able to grow in a medium containing canavanine. In the embodiment of this Figure, the deletion of the wild type gene is selected for; by comparison, in the embodiment of FIG. 1, the nonfunctional alleles 12 and 14 recombine to give rise to its respective wild type allele, which is selected for. The recombination occurs at a specified rate, which can be determined by methods to be discussed later on in this specification.

Other wild type allele 30's can also be used. Thus, for example, instead of the CAN1 gene, one can also use URA3, LYS2, and the like. When, for example, a strain containing the URA3 allele is present in construct 24 as the wild type allele 30, then the strain is unable to grow in a medium containing 5-fluoroorotic acid. As before, the alleles 26 and 28 recombine with each other to produce allele 32, and the strain containing allele 32 is able to grow in the presence of 5-fluoroorotic acid; see for one of the useful constructs E. Alani et al. "A method for gene disruption that allows repeated use of URA3 selection in the construction of multiply disrupted yeast strains", Genetics 116:541-545 (1987).

By way of further illustration, the CAN1 gene may be replaced by LYS2. When a strain containing the LYS2 allele is present in construct 24 as wild type allele 30, then the strain is unable to grow in a medium containing alpha-aminoadipic acid. As before, the alleles 26 and 28 recombine with each other to produce allele 32, and the strain containing allele 32 is able to grow in the presence of alpha-aminoadipic acid. See, e.g., an article by Barnes and Thorner entitled "Use of the LYS2 Gene for Gene Disruption", Gene Replacement, and Promoter Analysis in *Saccharomyces cerevisiae*, "Gene Manipulations in Fungi, "(Academic Press, Inc., 1985), the disclosure of which is hereby incorporated by reference into this specification.

Those in the art are aware of the identity of those media which select against various wild type 30 alleles. Thus, for example, an article by F. Winton et al. entitled "Eviction and Transplacement of Mutant Genes in Yeast" (Methods in Enzymology, 101:211-227 1983) discloses that a strain containing the URA3 gene cannot grow in medium containing 5-fluoroorotic acid. Thus, for example, an article by J. R. Broach et al. entitled "Development of a hybrid cloning vector and isolation of the CAN1 gene", (Gene 8:121-133, 1979) discloses that a strain containing the CAN1 gene cannot grow in the presence of canavanine; the article also describes the CAN1 gene which can be used as a wild type allele 30. These articles are hereby incorporated by reference into this specification.

With regard to the embodiment of FIG. 2, applicant has discussed the CAN1, URA3 and LYS2 wild type alleles 30. However, as those skilled in the art are aware, other genes can be used as long as they can be selected against with the use of a specified medium. These other genes and media are within the scope of this invention.

Figure 3:
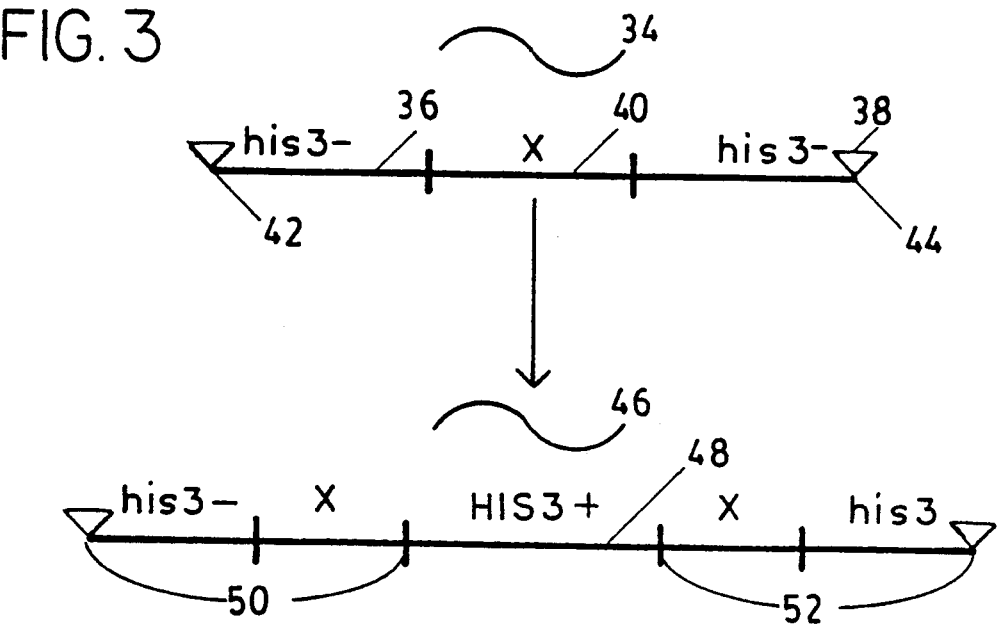

In the embodiment illustrated in FIG. 3, a construct 34 is illustrated which is comprised of two nonfunctional alleles, 36 and 38 and spacer DNA 40. As used in this specification, the term spacer DNA refers to any sequence of DNA which serves as a spacer between two repeated homologous elements. Points 42 and 44 indicate where deletions are present in the nonfunctional alleles. Thus, referring to the particular embodiment illustrated in FIG. 3, construct 34 is comprised of his 3−36, the homologous his3−38, and the spacer DNA 40; points 42 and 44 indicate where deletions have been constructed in vitro from the parent HIS3+ gene.

The construct of FIG. 3 is only one of many within the scope of this invention which can utilize at least two nonfunctional alleles. Thus, by way of illustration and not limitation, alleles 36 and 38 may be trp1−, leu2−, LEU2−, ura3−, lys2−, and the like. Thus, by way of illustration and not limitation, the spacer DNA 40 may be any DNA sequence but it is not essential for the system and thus it might be omitted without adverse affects.

In the construct of FIG. 3, an auxotrophic marker must be present. Thus, referring to FIG. 3, construct 34 contains two nonfunctional his3−alleles so that the strain requires histidine in the medium in order to grow. If one were to substitute ura3− for the his3−allele, the strain would require uracil to grow. If one were to substitute lys2− for the his3−alleles, the strain would require lysine to grow.

Construct 34 spontaneously undergoes genome rearrangement under ambient conditions to produce construct 46. See, for example, an article by M.T. Fasullo et al. entitled "Recombinational Substrates Designed to Study Recombination Between Unique and Repetitive Sequences in vitro", Proc. Natl. Acad. Sci, Volume 84, pp. 6215-6219 (September, 1987), the disclosure of which is hereby incorporated by reference into this case. It should be noted that this rearrangement involves the unequal pairing of the his3−alleles each one residing on one sister chromatid after DNA replication. After pairing, these alleles recombine with each other to yield construct 46. The rearrangement occurs at a certain rate under ambient conditions (at a rate of about $1 \times 10^{-6}$ per cell per generation), but the rate of the rearrangement is increased when the cell grows in the presence of many DNA damaging agents.

Construct 34 is unable to grow in the absence of histidine. If one had used, e.g., leu2− instead of his3− at positions 36 and 38, then the construct would have been unable to grow in the absence of leucine. The genome rearrangement which is favored by the presence of the DNA-damaging agents forms construct 46 which is able to grow in the absence of the histidine, or leucine, or whatever the strains containing the auxotrophic alleles 36 and 38 require to grow.

Unlike the constructs produced in FIGS. 1 and 2, the arrangement of alleles in construct 46, after the genome rearrangement, is comprised the wild type HIS3 allele 48 flanked by a duplication 50 and 52 of a portion of construct 34. It is believed that the rearrangement which occurs in this case involves unequal sister chromatid exchange or conversion. See, for example, the article by Fasullo et al. cited above.

Figure 4:
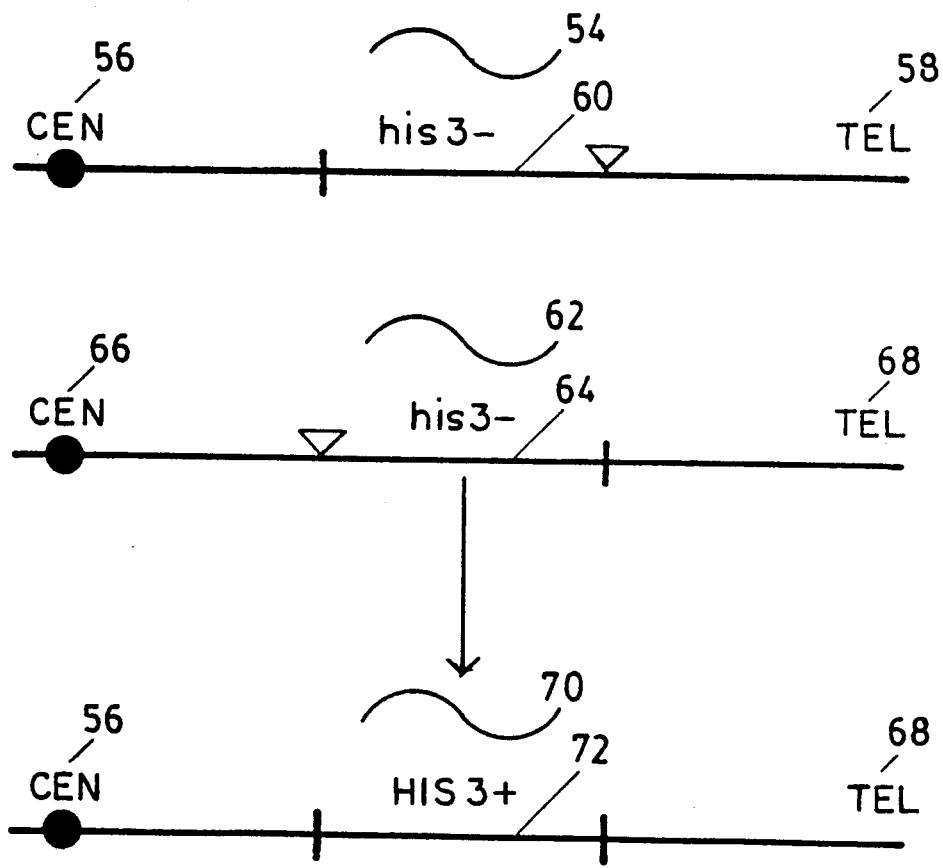

FIG. 4 illustrates yet another embodiment involving two homologous alleles which, unlike the constructs of FIGS. 1,2, and 3, each reside on different, nonhomologous chromosomes. Referring to FIG. 4, chromosome 54 is comprised of centromere 56 and telomere 58. As those in the art are aware, the term centromere refers to the spindle fiber attachment region of a chromosome. The term telomere refers to the region forming each end of the chromosome.

Referring again to FIG. 4, chromosome 54 is comprised of his3−allele 60. Nonhomologous chromosome 62 is comprised of his3−allele 64, centromere 66, and telomere 68. The chromosomes 54 and 62 are nonhomologous; the alleles 60 and 64 undergo recombination to give rise to the wild type HIS3 allele 72 on the hybrid chromosome 70, which comprises centromere 56 from chromosome 54 and telomere 68 from chromosome 62. This mechanism is known to those skilled in the art as translocation.

As is the case with the constructs of FIGS. 1-3, one can use other auxotrophic alleles of genes LEU2,TRP-1,URA3,LYS2, and the like.

Any nonhomologous chromosome pair can be used to provide chromosomes 54 and 62; there are 17 known such chromosomes in yeast.

The medium used in any particular situation wherein the construct of FIG. 4 will be used in the process should be the respective omission medium for the construct. If, e.g., alleles 60 and 64 are his3−, then a medium lacking histidine should be used. If, e.g., alleles 60 and 64 are ura3−, then the medium should be lacking uracil.

The constructs 54 and 62 are unable to grow in the absence of the respective growth factor. However, the construct 70 formed by the rearrangement is able to grow in the absence of the respective growth factor. The rearrangement occurs spontaneously under ambient conditions in the absence of DNA-damaging agents at a rate of about $1 \times 10^{-8}$ occurrence per cell per generation. See, for example, the Fasullo et al. article cited above.

Figure 5:
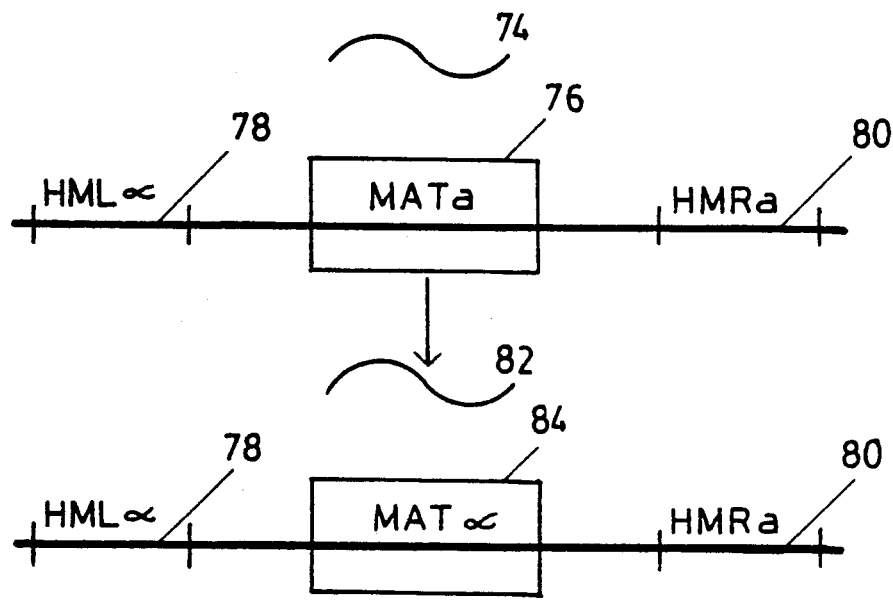

Yet another embodiment is illustrated in FIG. 5. Referring to FIG. 5, Chromosome 74 is a naturally-occurring chromosome which is found as "Chromosome III" in yeast. This chromosome 74 is comprised of MAT-a allele 76, which determines the mating type in yeast. The mating type switching system in heterothallic strains of *Saccharomyces cerevisiae* yeast is described in articles by Schiestl et al. entitled "X-Ray Enhances Mating Type Switching in Heterothallic Strains of *Saccharomyces cerevisiae*", (Mol. Gen. Genet., 186:512–517, 1982) and "Induction of Mating Type Interconversion in a Heterothallic Strain of *Saccharomyces cerevisiae* by DNA Damaging Agents", (Mol. Gen. Genet, 191:59–65, 1983). The disclosure of these Schiestl references is hereby incorporated by reference into this specification.

Chromosome 74 is also comprised of silent mating type loci 78 and 80, which are not expressed; thus, locus 78 can be HMLα, and locus 80 can be HMRa.

Alleles 78 and 76 on chromosome 74 can undergo recombination by unidirectional, intrachromosomal gene conversion to create chromosome 82 which is comprised of allele MATα. This change in the phenotype of the cell can be selected for in the presence of a tester strain expressing mating type a, which is unable to switch to type α.

A strain containing chromosome 74 is unable to mate with the tester strain to form a diploid which can grow in the medium described in the aforementioned Schiestl articles. However, a strain containing chromosome 82 can mate with the tester strain to form a diploid which can grow in the test medium. The conversion of chromosome 74 to chromosome 82 is favored by the presence of DNA damaging agents. See, e.g., the Schiestl papers.

In yet another preferred embodiment mammalian cells are used and the genetic events shown in FIGS. 1 to FIG. 4 can be in an equivalent fashion constructed with mammalian cells. The construction of such a system requires selectable markers for transformation of mammalian cells which are available. These selectable markers include the herpes simplex virus type 1 gene coding for thymidinekinase, H-TK, the neomycin (neo) gene of Tn5, which confers G418 resistance to transformed mammalian cells and the bacterial plasmid encoded hygromycin-B-phosphotransferase (hph) gene which confers resistance to hygromycin-B in mammalian cells and the like. For a description and a summary of the usefulness of these genes see e.g., a book by R. Kucherlapati entitled "Gene Transfer", Plenum Press, New York, the disclosure of which is hereby incorporated into this specification. The H-TK, neo and the hph genes are freely available to those skilled in the art and are present in the collection of GeneBioMed, Inc., of 509 Highland Ave, Rochester, N.Y. 14620. Transformation of mammalian cells can be accomplished by CaPO$_4$-DNA mediated gene transfer, and methods to derive single copy integrants have been described see e.g., the aforementioned book by Kucherlapati. Processes to screen for homologous intrachromosomal recombination in mammalian cells have been developed with systems other than the ones analogous to FIGS. 1 to 4, see e.g., Letsou and Liskay on pages 383–409 in the aforementioned book by Kucherlapati.

The systems in mammalian cells can be constructed by replacing the genes LEU2, TRP1, URA3, LYS2, and the like of yeast with the aforementioned selectable dominant markers HTK, neo and hph of mammalian cells. The HTK system allows to select positively for the TK+ phenotype on medium supplemented with hypoxanthine, aminopterin and thymidine (HAT medium) and negatively for the TK− phenotype on medium supplemented with hypoxanthine and bromodeoxyuridine (HBu medium) so that it allows determination of recombination events by selection for the presence of the gene as in FIGS. 1, 3 and 4 as well as selection against the presence of the gene as in FIG. 2. The neo gene can be selected for on medium supplemented with G418 and the hph gene can be selected for on medium supplemented with hygromycin-B. The neo and the hph genes can be used for constructs analogous to FIGS. 1, 3 and 4.

One preferred class of constructs for use in applicant's process are those described in FIG. 1 and in that portion of the specification which corresponds to FIG. 1. In this portion of the specification, a detailed description will be given of how to construct one of the embodiments of construct 10, it being understood that this description is equally applicable to other embodiments of construct 10.

Figure 6:
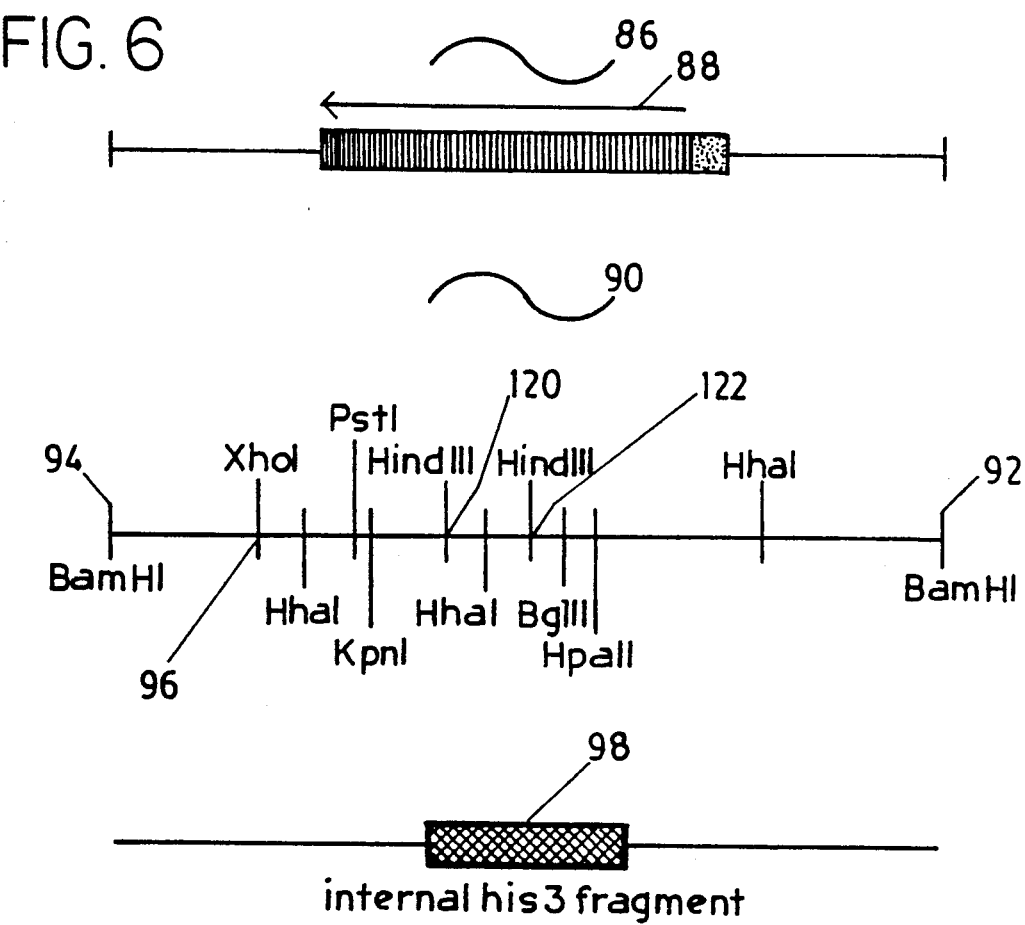
FIG. 6 is a schematic of the structure of the selectable gene used in the preferred embodiment shown in FIG. 1.

Referring to FIG. 6, 86 and 90 represent the restriction map of the HIS3+ gene. As those in the art are aware, a restriction enzyme digests or cuts DNA at certain recognition sequences, i.e., certain sites in the DNA molecule where the base sequence is recognized by the enzyme. Some restriction enzymes and the sites they recognize on the DNA are described on pages 110–111 of the aforementioned Goodenough book.

The direction of the gene is shown by arrow 88, which indicates in which direction the gene is transcribed by the RNA polymerase.

Map 90 shows the location of the recognition sequences of the restriction enzymes shown within the fragment. Thus, Bam HI will recognize and cut at points 92 and 94 at the borders of the fragment 86. Thus, for example, Xho I will recognize and cut within fragment 86 at point 96.

In the process of producing one of the preferred embodiments used in the invention, the HIS3+ gene is cut by restriction enzymes to produce internal his3−− fragment 98 which was used in this embodiment.

Figure 7:
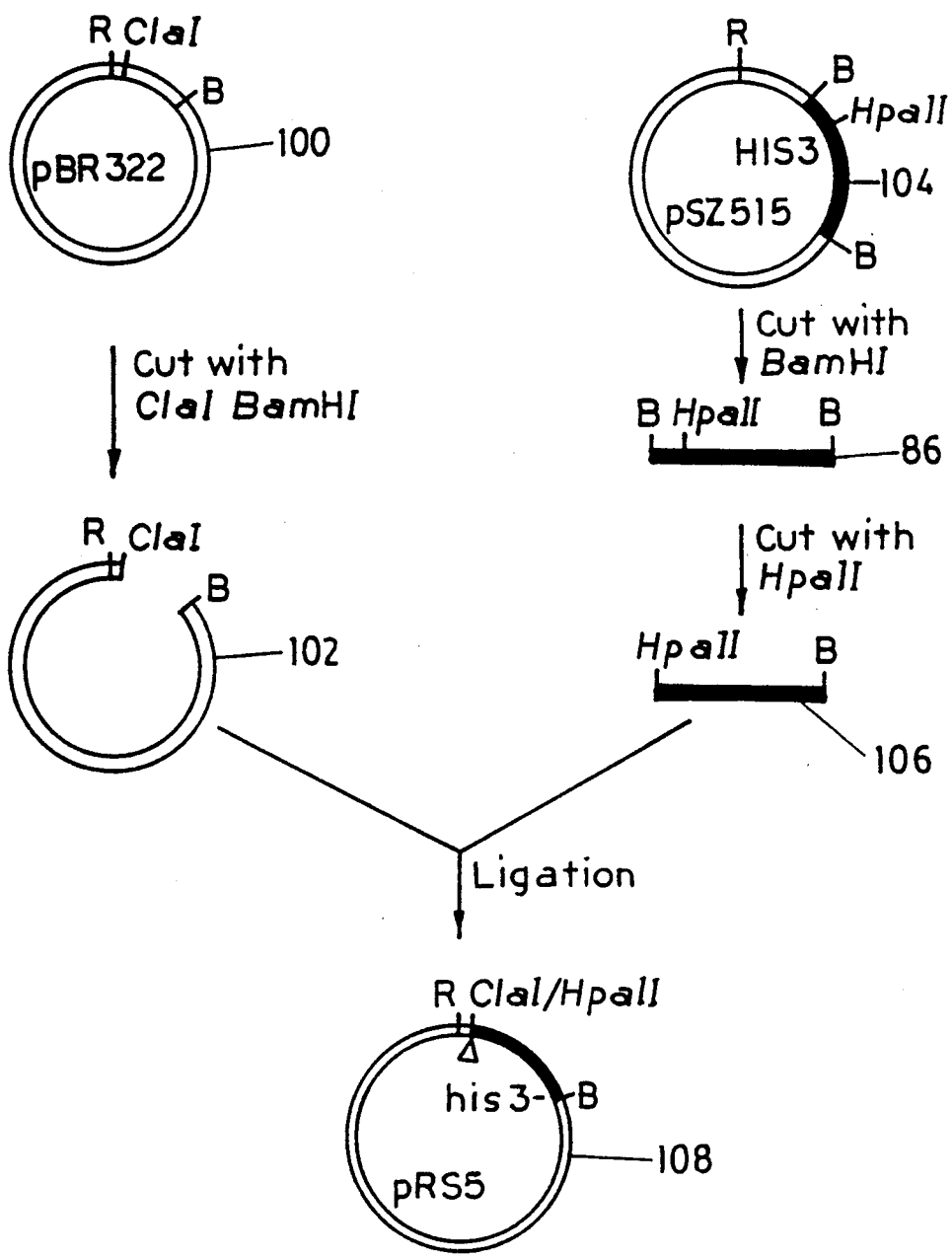
FIG. 7 is a schematic of the construction process of an intermediate plasmid used in the preferred embodiment shown in FIG. 1.
Figure 8:
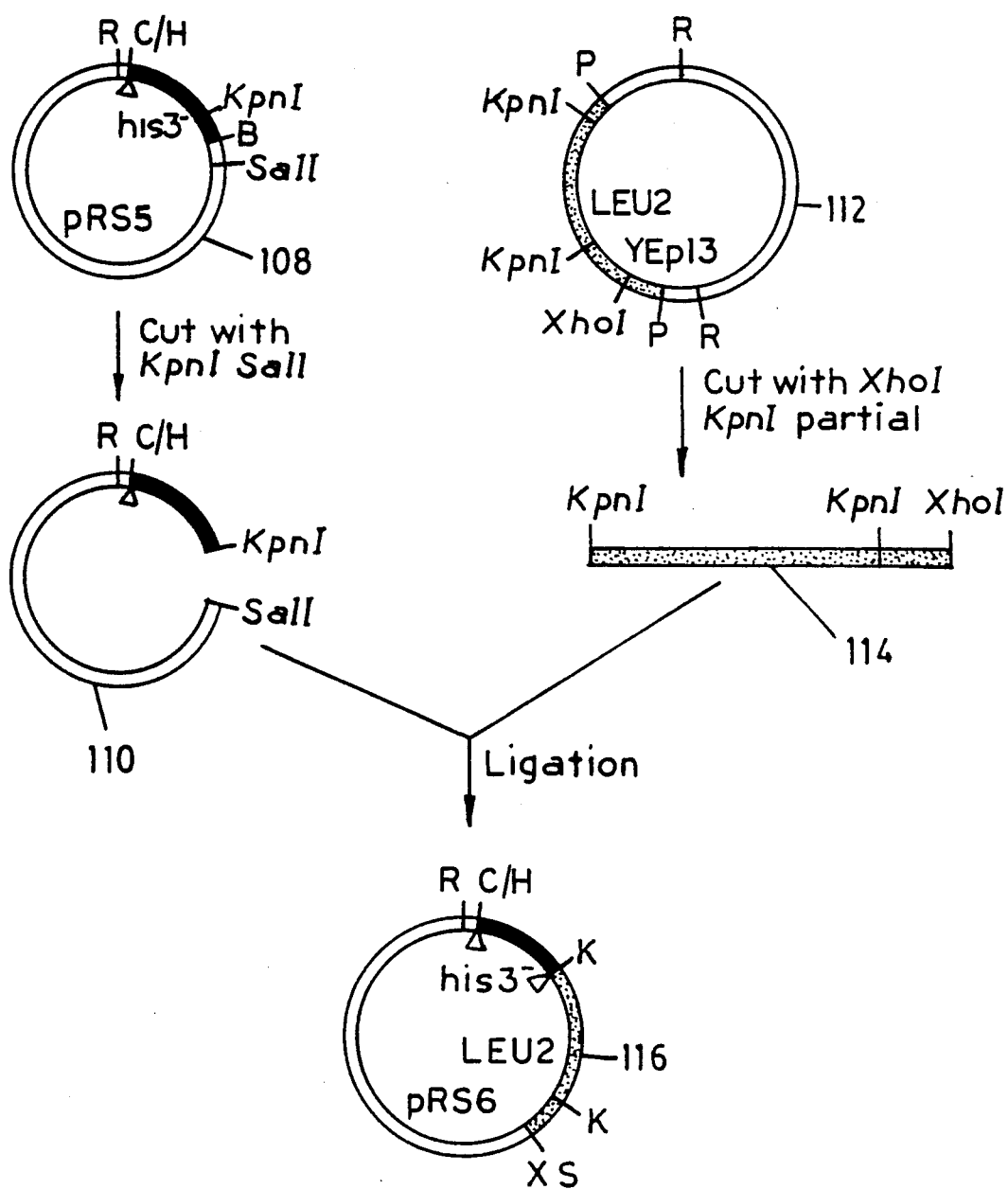
FIG. 8 is a schematic of the construction process of the plasmid used in the preferred embodiment shown in FIG. 1 using the intermediate structure shown in FIG. 7.

FIGS. 7 and 8 illustrate how the plasmid pRS6 is constructed, which contains the internal fragment 98. *Escherichia coli* SF8 containing plasmid pRS6 was deposited on Nov. 30, 1987 with the American Type Culture Collection of 12301 Parklawn Drive, Rockville, Md. as number 67568 by GeneBioMed, Inc. It is believed that strain SF8 has the following genotype: hsdr-, hsdm-, recA1, supE44, lacz4, leuB6, proA2, and thi1.

In FIGS. 7 and 8, the terms "R" and "B" indicate the sites of restriction enzymes Eco RI and Bam HI, respectively.

Plasmid pBR322 is readily available to those skilled in the art. Its construction is described in an article by F. Bolivar et al. entitled "Construction and Characterization of New Cloning Vehicles, II. A Multipurpose Cloning System", (Gene 2:95, 1977). Plasmid pSZ515 also is readily available; its construction is described in a publication by Orr-Weaver et al. entitled "Yeast transformation: a model system for the study of recombination", Proc. Natl. Acad. Sci. USA, 78:6354–6358, 1981); and applicant obtained this plasmid from Dr. J. Szostak, one of the authors of said article. These references are hereby incorporated by reference into this specification. It should be noted that the Orr-Weaver reference also discloses the preparation of other plasmids.

As will be readily available to those skilled in the art, plasmids pBR322 and pSZ515 were chosen by the applicant in order to construct a certain allele as intermediate, pRS5. When other constructs are desired, other plasmids can be used as starting materials. As is well known to those in the art, these other plasmids are readily available, and their construction is well known to those in the art. See, for example, the aforementioned Orr-Weaver publication.

Referring again to FIG. 7, Plasmid 100 (pBR322) was digested with restriction enzymes ClaI and BamHI, and the larger of the two resulting fragments, fragment 102, was isolated.

The procedure for digesting plasmids with restriction enzymes and of isolating the fragments so digested is well known to those skilled in the art. Thus, by way of illustration and not limitation, one may refer to a publication by T. Maniatis et al. entitled "Molecular Cloning: A Laboratory Manual", (Cold Spring Harbor Laboratory, Cold Spring Harbor, N.Y., 1982). In the Maniatis Laboratory Manual, restriction enzymes are disclosed on pages 97–107, and the isolation of gene fragments by Gel Electrophoresis is described on pages 149–186. The Maniatis Laboratory Manual is hereby incorporated by reference in its entirely into this specification.

Referring again to FIG. 7, the restriction enzyme digest was electrophoresed on a agarose gel containing 0.7 percent agarose and TBE buffer containing 0.089 molar Tris Base, 0.089 molar boric acid, and 0.01 molar disodium ethylene diamine tetra-acetate dihydrate (EDTA). This electrophoresis buffer is described on page 454 of the aforementioned Maniatis Laboratory Manual.

The electrophoresis was carried out with a current of 30 volts for about 8 hours, and the DNA fragments were stained with ethidium bromide; the ethidium bromide was used at a concentration of 0.5 micrograms per milliliter of buffer solution.

The fragments were visualized under ultra-violet light with a frequency of 300 nanometers. Isolation was then carried out in accordance with the procedure of Dretzten et al., "A reliable method for the recovery of DNA fragments from agarose and acrylamide gels", Anal. Biochem. 112:295–298 (1981), the disclosure of which is hereby incorporated by reference into this specification. The procedure described by Dretzten is also mentioned on pages 168–169 of the aforementioned Maniatis Laboratory Manual. In this procedure, the DNA is collected by binding it to DEAE-cellulose paper and by elution from the paper.

Plasmid 104 (pSZ515) was cut with restriction enzyme BamHI, and fragment 86 was isolated (see FIG. 6) in substantial accordance with the procedure described for plasmid 100. The isolated fragment 86 was further digested by restriction enzyme HpaII, and fragment 106 was isolated. The restriction and isolation procedures used were similar to those described above.

Fragments 102 and 106 were ligated with DNA ligase purchased from the Bethesda Research Laboratory, of Gaithersburg, Md. The ligation procedure is well known to those skilled in the art and is described, in, e.g., pages 286 to 307 of the aforementioned Maniatis Laboratory Manual. The particular ligation buffer used is described on page 474 of the Maniatis Laboratory Manual. This buffer contained 0.66 moles of Tris base buffered to a pH of 7.5 with hydrochloric acid, 50 millimolar of magnesium chloride, 50 millimolar of dithiothreitol, and 10 millimolar of adenosine triphosphate.

With this ligation, the *E. coli* strain SF8 was transformed, and ampicillin-resistant colonies containing the plasmid pRS5 (108) were isolated. The construct pRS5 was verified by restriction analysis (see, e.g., pages 363–402 of the Maniatis Laboratory Manual).

Referring now to FIG. 8, plasmid construct 108 was digested with restriction enzymes KpnI and SalI, and large fragment 110 was isolated in accordance with the isolation procedure described above. Plasmid YEp13 (112) also was digested. This plasmid is readily available and was constructed as described in the procedure described in the aforementioned Broach et al. article which appears in Gene 8:121–133 (1979).

Plasmid 112 was digested with XhoI and partially with KpnI, and fragment 114 was isolated in accordance with the aforementioned procedure. Fragments 110 and 114 were then ligated in accordance with the procedure described above to produce plasmid pRS6 (116), which as deposited on Nov. 30, 1987 as "*Escherichia coli*. SF8 containing plasmid pRS6", number 67568, with the American Type Culture Collection, 12301 Parklawn Drive, Rockville, Md. 20852 by GeneBioMed, Inc. of Rochester, N.Y.

Figure 9:
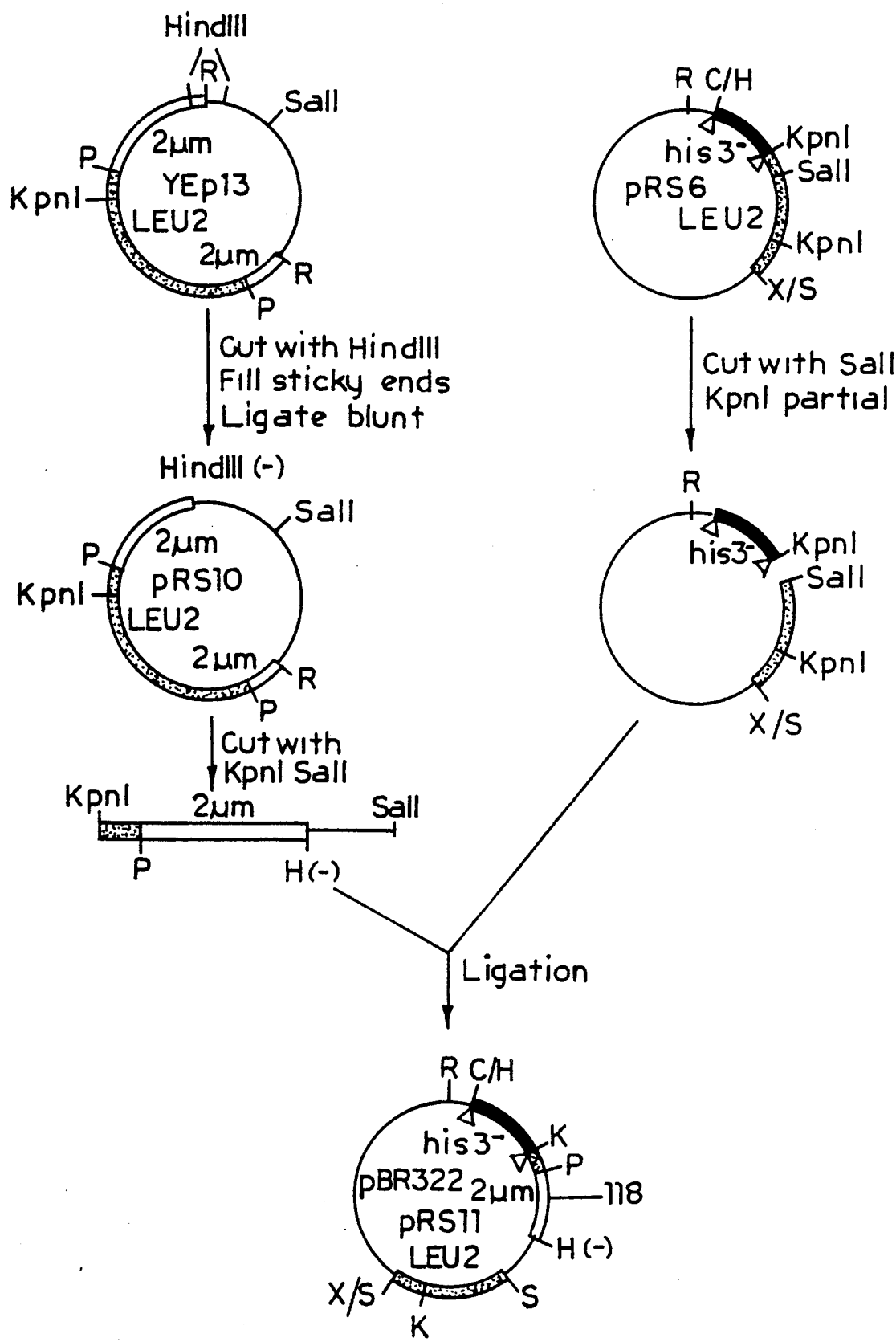
FIG. 9 is a schematic of the construction process of the plasmid used for the characterization of the preferred embodiment shown in FIG. 1.

FIG. 9 illustrates a process for evaluating the mechanism by which recombination used in this preferred embodiment is believed to take place. This figure is presented to merely illustrate applicant's theory as to how said mechanism takes place; however, applicant does not wish to be bound to any particular theory. As reference to FIG. 9 will illustrate, pRS11 used for the purpose of illustrating the mechanism was constructed by incorporation of the yeast origin of replication from the 2 micron plasmid into plasmid pRS6 (construct 116) to produce plasmid pRS11 (118). See, e.g., an article by J. R. Broach entitled "The yeast plasmid 2 mm circle", appearing in a book by J. N. Strathern et al. entitled "The Molecular Biology of the Yeast Saccharomyces: Life Cycle and Inheritance" (Cold Spring Harbor Press, Cold Spring Harbor, N.Y., 1981), the disclosure of which is hereby incorporated by reference into this case.

Figure 10:
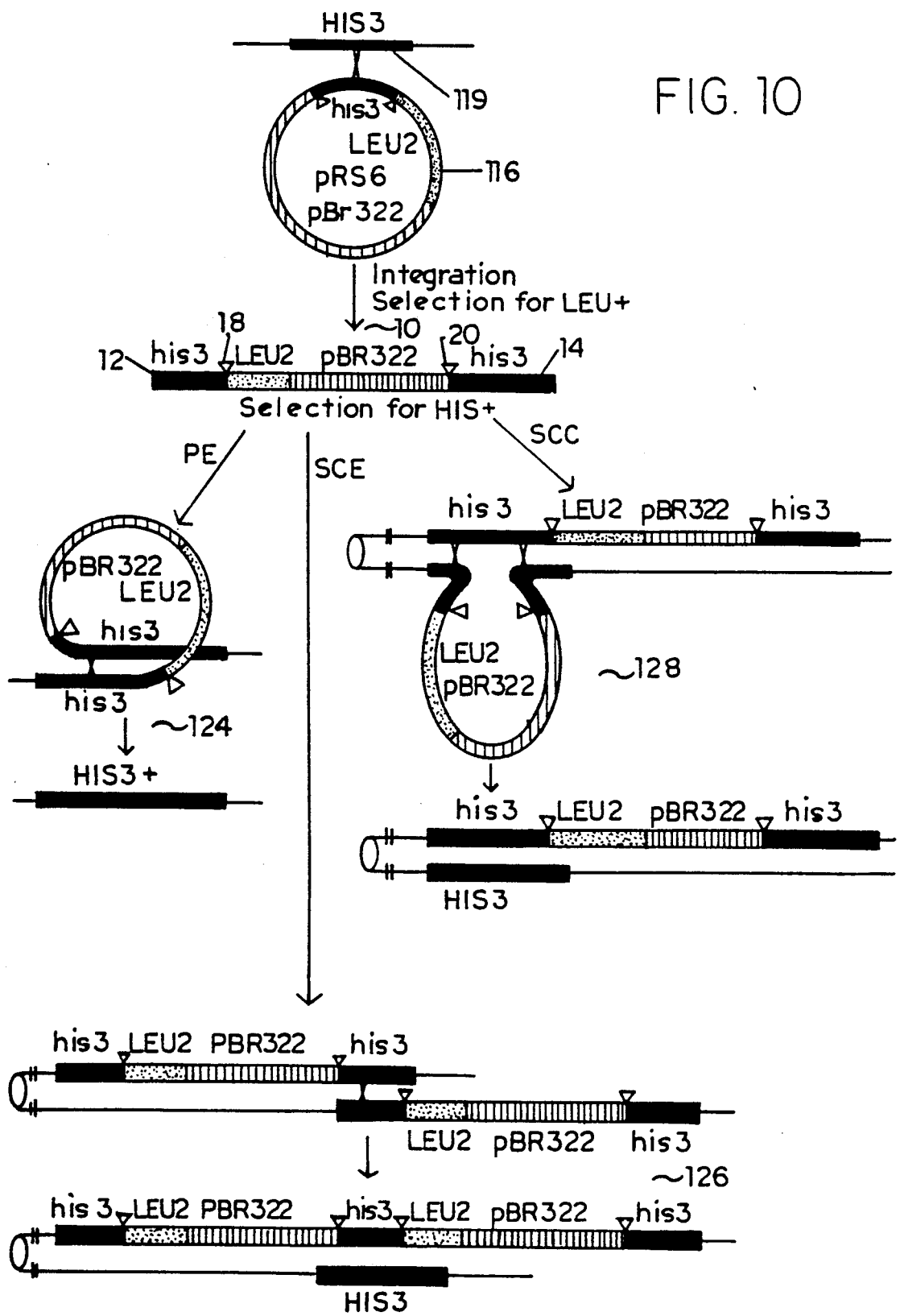
FIG. 10 is a schematic of the characterization of the preferred embodiment shown in FIG. 1 used to identify the nature of the recombination between the repeated elements.

FIG. 10 illustrates the construction and use of construct 10. A strain containing construct 10 was deposited as "*Saccharomyces cerevisiae* RSY6" on Nov. 30, 1987, number 20871, with the American Type Culture Collection of Rockville, Md. by GeneBioMed, Inc.

Referring to FIG. 10, plasmid 116 was digested with HindIII to produce a small gap within the internal fragment of his3; the HindIII gap is illustrated in FIG. 6 at points 120 and 122. Digestion was conducted in substantial accordance with the procedure described above.

A yeast strain with marker leu2$^-$ was used. As will be apparent to those skilled in the art, any yeast strain which is leu2$^-$HIS3$^+$ can be used. The particular yeast strain used by the applicant was S35/2−10C, which had the following genotype: MATa, ura3−52, leu2−3,112, trp5−27, arg4−3, ade2−40, and ilv1−92.

The yeast strain S35/2−10C was transformed with the digested plasmid 116 (pRS6), and colonies able to grow on media lacking leucine were isolated. This isolation procedure was conducted in accordance with the procedure of the F. Sherman article ("Methods in yeast genetics . . .", 1986) described above.

Plasmids which contain a double-strand gap in a region homologous to a yeast sequence recombine with their homologous sequence, thus producing integration or transplacement events, depending on the plasmid or sequence used. See, e.g., Orr-Weaver et al., "Genetic Applications of yeast transformation with linear and gapped plasmids", Methods Enzymol. 101:228-245 (1983), the disclosure of which is hereby incorporated by reference into this specification. This phenomenon is illustrated in FIG. 10, wherein plasmid 116 is integrated into yeast HIS3 gene 119 to produce construct 10. This process involves disruption of wild type allele 119 to give rise to construct 10, which contains deletion his3 alleles 12 and 14 resulting from the disruption of allele 119. It should be noted that construct 10 contains delections 18 and 20.

The constructs of FIGS. 1-5 may be used to detect the presence of chemicals which cause genome rearrangement. The procedure for so using these constructs is described below with regard to the construct of FIGS. 1-4.

It appears that at least the most preferred constructs of this invention are substantially more sensitive in detecting carcinogenic chemicals than are prior art short term tests. Thus, as is illustrated in Example 3 of this specification, when the construct of FIG. 1 is used in the process of this invention, chemicals such as formaldehyde, safrole, eugenol, urethane, aminoantipyrine, ethionine and the like test positive in the system. Although safrole, urethane, aminoantipyrine and ethionine are all known carcinogens, every one of them tests negative in the widely used prior art short term tests, including the "Ames Assay", systems screening for chromosomal aberrations and sister chromatid exchange in mammalian cells or cultures and others. See, for example, H. A. Milman and E. K. Weisburger's "Handbook of Carcinogen Testing", (Noyes Publications, Park Ridge, N.J., 1985), pages 100-115, the disclosure of which is hereby incorporated by reference into this specification. Formaldehyde is another known carcinogen and is negative in the "Ames Assay" as well as in many other short term tests.

The process of this invention can be used to screen for any agent which is suspected of causing genome rearrangement. The agent may be in gaseous, liquid, or solid form; it may be an electromagnetic wave; it may be an element or a compound; or it may be some combination thereof.

The suspected agent may be radiation such as, e.g., radiation with a frequency of from $3 \times 10^0$ to $3 \times 10^{22}$. Some of the radiations which are suspected of causing genome rearrangement include, by way of illustration, ultra-violet light, X-rays, gamma-rays, and the like. Often the suspected agent may be a combination of one or more forms of radiation with one or more other agents. Thus, for example, the interaction of X-rays with certain organic matter is believed to often create free radicals which interact with DNA and are believed to cause DNA lesions.

The suspected agent may be any material or form of energy. Some of the agents which the process of this invention can be used to screen are described in a book by H. A. Milman and E. K. Weisburger entitled "Handbook of Carcinogen Testing", (Noyes Publications, Park Ridge, N.J., 1985), the disclosure of which is hereby incorporated by reference into this specification.

In one preferred embodiment, the agent to be tested is one which is not carcinogenic by itself but becomes carcinogenic when metabolized. These agents are often referred to as "procarcinogens" and are described, e.g., on pages 130-149 of said Milman and Weisburger handbook.

When a suspected procarcinogen is to be tested in the process of this invention, one should first provide a medium designed to simulate the metabolism the procarcinogen is subjected to in the body. Thus, for example, for a procarcinogen which can be metabolized in the presence of liver enzymes, one can provide a medium comprised of liver enzymes.

By way of illustration, one can provide a medium comprised of 10 percent (by volume) of "S9" (a supernatant of liver homogenate which is described in the aforementioned paper by Ames et al. appearing at pages 347-364 of volume 31, (1975) of Mutation Research entitled "Method for Detecting Carcinogens and Mutagens with the Salmonella/Microsome Mutagenicity Test: and which, as is known to those skilled in the art, is commercially available.), 2 percent by volume of a solution comprising magnesium chloride and potassium chloride, 0.5 percent by volume of a one molar solution of glucose-6-phosphate, 4 percent by volume of nicotineamide adenine dinucleotide phosphate, 50 percent by volume of a 0.2 molar phosphate buffer with a pH of 7.4, and 35.5 percent by volume of water. This S-9 mix is described in detail in 1975 Ames et al. paper.

As those in the art are aware, the S-9 mix should be evaluated to determine that it is active. It is preferred that, when the procarcinogen is being evaluated, a control experiment utilizing the S-9 mix and a known procarcinogen is conducted to verify that the S-9 mix is active.

In this embodiment, the harvested yeast cells are incubated in the presence of both the S-9 mix and the suspected procarcinogen.

In the first step of this process, a viable species of Saccharomyces cerevisiae yeast which comprises repeated genetic elements in its haploid genome is provided. The provision of this species of yeast is described in the first portion of this specification.

It is preferred to grow the viable species of yeast in suitable growth medium in order to have a sufficient number of yeast cells so that the experimental data generated will be statistically significant.

In order to generate a suitable number of the viable yeast cells, the cells should be grown in a medium which permits growth of the cells which did not undergo genome rearrangement. Those skilled in the art are well aware of suitable media which will permit growth of the cells which did not undergo genome rearrangement.

A suitable medium for permitting growth of the cells which did not undergo genome rearrangement is "YEPD". This medium contains yeast extract (one percent, by weight), peptone (any of various protein compounds obtained by acid or enzyme hydrolysis of natural protein, which is present in a concentration of 2 percent, by weight), dextrose (2.0 percent by weight), agar (2 percent by weight), and water. For each and every one of the constructs described in FIGS. 1-5, this medium permits the growth of all cells. Other such media known to those skilled in the art also may be used for this purpose such as, e.g., "synthetic complete medium".

Synthetic complete medium contains yeast nitrogen base without amino acids and with ammonium sulfate, (0.67 percent, by weight, which can be purchased from Difco Laboratories of Detroit, Mich., dextrose (2 weight percent), agar (2 weight percent), water, and the following amino acids and bases per liter of total solution: 20 milligrams each of L-trypthophan, L-histidine hydrochloride, L-arginine hydrochloride, L-methionine, L-isoleucine, L-tyrosine, L-lysine hydrochloride, adenine sulfate, and uracil; 30 milligrams per liter of total solution of L-leucine; 350 milligrams of L-threonine per liter of solution; and 75 milligrams per liter of L-valine.

Other suitable growth media can also be used. Thus ommissions, and/or additions may be made in the concentrations and/or the compositions of the media described above without adversely affecting their performance.

After cells containing the construct of this invention have been grown to a suitably large number, it is preferred to purify the cells so obtained by means well known to those in the art. Thus, for example, one can collect cells by centrifugation or filtration; see, e.g., the article by F. Sherman et al. Other suitable separation processes also can be used. Optionally, the yeast cells may be washed with suitable solution(s).

It is preferred that, after the yeast cells have been harvested, they are counted in order to determine the number of yeast cells per unit of buffered solution. Conventional means well known to those skilled in the art can be used to count the yeast cells. Thus, by way of illustration, one can use a hemocytometer (a conventional means of counting read blood cells).

It is preferred to conduct a preliminary experiment to determine those concentrations of the agent to be tested which should be evaluated in the main experiment. Yeast cells are exposed to a wide range of concentrations of the agent to be tested to determine its cytotoxicity.

Suitable concentrations of the agent are used for its evaluation. Several portions of the harvested yeast cells are used in the experiment. One portion, which is otherwise treated in exactly the same way as the exposed portions, is not exposed to the agent. The other portions of the harvested yeast cells are exposed to the agent at various concentrations. Alternatively, and/or additionally, controlled-variable tests can be conducted with various concentrations of the yeast cells as well as various concentrations of the agent. As is known to those skilled in the art, the concentration of the yeast cells might influence the effect of the agent in one or more ways; thus, for example, a dense solution of yeast cells might shield irradiation more effectively than a dilute solution.

The separated yeast cells can be exposed to the agent to be tested by various means. In one embodiment, the yeast cells are mixed with a buffer before such exposure. In another embodiment, the yeast cells are mixed with a buffer, and the mixture is then plated directly onto the selection medium before being exposed to the agent. In yet another embodiment, the yeast cells are grown in a growth medium (such as one or more of the media described above which permit the growth of the cells which have not undergone genome rearrangement) in the presence of the agent to be tested.

In the most preferred embodiment it is preferable to grow the cells in a medium which selects against the occurrence of the genome rearrangement to keep the control values as low as possible. In the embodiment described in FIG. 1 it is shown that the LEU2 gene of construct 10 is lost after the genome rearrangement which results in construct 22. Therefore cells containing construct 10, before the rearrangement are able to grow in the absence of leucine in the medium, but cells containing construct 22, after the genome rearrangement are not able to grow in the absence of leucine. After the genome rearrangement cells containing construct 22 are able to grow in the absence of histidine in the medium, but cells containing construct 10 before the genome rearrangement are not able to grow in the absence of histidine. Therefore the selection scheme which was used for Example 3 involves growth of the yeast culture in medium lacking leucine but containing histidine before and during the exposure to the potential carcinogens or other test agents. After the exposure the cells which have undergone genome rearrangement are selected on medium lacking histidine but containing leucine.

It is preferred that, when the cells are to be grown in the presence of the agent, logarithmic phase cultures are used. In one embodiment, for each of the test strains, a cell suspension of $2 \times 10^6$ cells per milliliter—LEU medium be prepared from a logarithmic phase culture pregrown in liquid—LEU medium. The whole mix is aliquoted into portions of 5 milliliter into disposable plastic tubes in the presence of the agent to be tested, the tubes are sealed and shaken continuously for 17 hours.

When the yeast to be used is mixed with a buffer, a suitable buffer which is compatible with the agent to be tested should be used. Thus, for example, nitrous acid needs an acidic pH to be a mutagen; and the buffer chosen for the yeast cells thus should be acidic.

When the yeast cells are to be plated upon a suitable selection medium and exposed to the agent, a medium which is both compatible with the agent and which promotes selection for genome rearrangement should be used.

The yeast cells are then exposed to the agent or agents to be tested. In general, the exposure is conducted under conditions and for a time sufficient to simulate the environment which is being tested for. Thus, e.g., a wide range of reagent concentrations and exposure times is disclosed in said Milman and Weisburger book; they all may be used in the process of this invention under suitable circumstances.

The exposed yeast cells are characterized by comprising repeated genetic elements in their haploid genomes, which elements are preferably selected from the group consisting of functional and nonfunctional genetic elements. These repeated genetic elements are sufficiently homologous so that, under ambient conditions, they give rise to genome rearrangement which is identifiable, i.e., when they are present in suitable media they can be distinguished from cells which have not undergone the genome rearrangement. In one preferred embodiment, the genome rearrangement involved with the exposed yeast cells is a deletion. In another preferred embodiment, the genome rearrangement involved is a duplication. In yet another embodiment, the genome rearrangement involved is a translocation. In yet another embodiment, the genome rearrangement involved is intrachromosomal gene conversion. Regardless of whether the genome rearrangement occurs by deletion or duplication or translocation, the screening procedure described below can be used.

A selection medium is selected for the yeast strain which, after the yeast cells have been plated onto it and grown, enables one to identify those yeast cells which have undergone the specified genome rearrangement. Those skilled in the art are aware of many such growth media which facilitate the identification of such yeast cells.

Thus, by way of illustration and not limitation, many such media are described in F. Sherman et al.'s "Methods in yeast genetics, a laboratory manual" (Cold Spring Harbor Laboratory, Cold Spring Harbor, N.Y., 1986).

As those skilled in the art are aware, each construct requires a certain selection medium which will enable one to identify the cells which have undergone genome rearrangement.

By way of illustration, with the constructs of FIGS. 1, 3, and 4, one can use histidine omission medium (medium lacking histidine) for a construct utilizing one gene in the histidine metabolic pathway as repeated genetic elements. Thus, for example, the L-histidine hydrochloride may be omitted from the synthetic complete medium described elsewhere in this specification to provide a medium which contains all growth factors except L-histidine. Likewise, for these constructs, one can use leucine omission medium for a construct utilizing one of the genes in the leucine metabolic pathway.

As those in the art are aware, some selection media can be used to select for the gain of a function which can arise, e.g., by reversion of a disrupted gene; see, for example, FIGS. 1, 3, and 4. Alternatively, other selection media can be used to select against the presence of one or more genes; see, for example, FIG. 2. Thus, by way of illustration, the selection media may comprise an antibiotic which inhibits the growth of cells containing the gene which is selected against.

After the yeast cells have been exposed to both the agent to be tested and the selection medium under the conditions of the test and have been incubated for some time period of about more than one day preferably at 30 degrees Celsius or any other temperature which allows growth of the yeast cells used, the number of colonies formed by cells which have undergone genome rearrangement are counted and compared with the number of colonies of yeast cells identical in substantially every respect with the exception of not having been exposed to the suspected carcinogenic agent. The rates of genome rearrangement for both the control and experimental samples are then compared.

The experiments should be conducted at different concentrations of the agent to be tested. If the rate of genome rearrangement of the yeast cells consistently increases with increases in the concentration and/or exposure time of the agent to be tested, then this is one indication that such agent causes genome rearrangement and might be carcinogenic. If, additionally, the rate of genome rearrangement in the presence of one or more concentrations of the agent is substantially greater than the rate in the absence of the agent, this is yet another indication that such agent might be carcinogenic. It should be noted that the rate of increase of genome rearrangement is not necessarily linear with every agent and that some agents might show a lower rate of genome rearrangement with higher concentrations than with lower concentrations. As long as, for at least a certain range of the agent's concentrations, the rate of genome rearrangement is substantially greater than the rate obtained with the control samples, there is some indication that the agent might be carcinogenic.

Several factors influence what will constitute a "substantially greater" rate of genome rearrangement in the process. In the first place, the greater the number of yeast colonies obtained in the experiment, the lower the difference must be in order to be "substantial". In the second place, if a plot of the rate of genome rearrangement versus concentration of the agent to be tested produces a curve in which, for any two points, the rate of genome rearrangement for the higher concentration of agent is at least equal (and preferably higher than) the rate of rearrangement obtained with the lower concentration the increase might be regarded as substantial. This curve is to be distinguished from a curve obtained in which the rate of genome rearrangement does not consistently increase or at least stay the same as the concentration of the agent is increased. As those skilled in the art are aware, the yeast cell colonies can be counted by conventional counting means. Thus, for example, one may count these colonies by hand. Alternatively, one may utilize commercially available counters such as, e.g., the Artek counter.

The data obtained from the counting of the yeast cells may be evaluated by means well known to those skilled in the art. Thus, for example, one may use the procedures described in an article by B. Kunz and R. Haynes published in a book by J. Strathern entitled "The molecular biology of the yeast Saccharomyces", (Cold Spring Harbor Laboratories, Cold Spring Harbor, N. Y., 1981). Thus, e.g., one may use the procedures described in an article by F. Eckardt and R. H. Haynes entitled "Quantitative measures of mutagenicity and mutability based on mutant yield data", Mutation Res 74:439-458 (1980). The disclosure of these articles is hereby incorporated by reference into this specification.

The most preferred embodiment within the scope of this invention does have the advantage that the basis frequency obtained with the control shows better reproducibility than the control values obtained with other recombination systems in yeast. This is because the preferred medium used for precultivation of the cells selects against the genome rearrangement so that only the spontaneous frequency, which is in this case similar to the rate, is obtained. Thus the effect known as "Jack pot" to those skilled in the art is avoided.

CHARACTERIZATION OF THE PREFERRED SYSTEM TO TEST FOR GENOME REARRANGEMENT

This section is presented to illustrate the most preferred embodiment of this invention but is not to be deemed limitative thereof. This section in its entirety relates to the most preferred embodiment of this invention, which is illustrated in FIG. 1. Unless otherwise stated, all parts are by weight and all temperatures are in degrees centigrade.

Plasmids were constructed as substrates to study intrachromosomal recombination; see an earlier part of the specification and Example 1. The plasmids pRS6 (FIG. 7, construct 108) and pRS11 (FIG. 9, construct 118) both contained an internal fragment of the HIS3 gene as well as one selectable marker (LEU2). pRS11 in addition contained the 2 $\mu$m origin of replication to select for the presence of the plasmid after plasmid excision. pRS11FRT-had the FLP recombination site disrupted (see Example 1). Yeast strains RSY6 containing construct 10, RSY11 containing construct 118 and RSY11FRT- (see Example 1) were used. They contained the respective pRS plasmids integrated into the HIS3 gene of strain S35/2-10C giving rise to disruptions of the HIS3 gene construct 10 or analogs to it (FIG. 10). The two resulting his3 deletion alleles (FIG. 10) shared about 400 basepairs of homology and thus could interact with each other by homologous recombination. Reversion of his− to HIS+ occurred at a frequency of about $4\times10^{-4}$ in all three strains. All of 100 tested HIS+ revertants of strain RSY6 were leu−. Because of this observation strains used for recombination studies were always pregrown on −LEU medium to prevent growth of HIS+ revertants. Therefore the frequency of HIS+ revertants is a measure of the recombination rate.

Reversion of the gene disruption produced by integration of pRS6 into the HIS3 locus (FIG. 10) could theoretically come about by three different mechanisms. The mechanisms include reciprocal crossing over between two his3 deletion alleles in G1 or on one chromatid in G2 (PE, event 124, FIG. 10) as well as unequal sister chromatid exchange (SCE, event 126 FIG. 10) and conversion (SCC, event 128, FIG. 10). The study was aimed at defining which one of the above mechanisms was involved in reversion of the gene disruption at HIS3.

If plasmid excision (PE, event 124, FIG. 10) was the main mechanism for reversion the frequency of PE should be similar to the frequency of the overall reversion events. Because the integrated plasmid pRS11 contained an origin of replication as well as one selectable marker following excision, the plasmid should become established in the cells in high copy number. Sister chromatid exchange (SCE, event 126, FIG. 10) and conversion (SCC, event 128, FIG. 10) differ from each other in their reciprocal product. After SCE the reciprocal product should contain a duplication of the integrated plasmid whereas after SCC the reciprocal product should remain a single integrant (FIG. 10).

The 2 μm plasmid contained an origin of replication and is most likely located in the nucleus (see for review: Broach, "The yeast plasmid 2 μm circle. pp. 445–470. In *The Molecular Biology of the Yeast Saccharomyces: Life Cycle and Inheritance*. Edited by J. N. Strathern, et al. Cold Spring Harbor Laboratory Press, Cold Spring Harbor, N.Y., 1981). Volkert and Broach in a publication entitled "Site specific recombination promotes plasmid amplification in yeast." Cell 46:541–550 (1986) have shown that the 2 μm plasmid can establish itself in high copy number in most of the cells after a single copy has been excised from the chromosome. They integrated one 2 μm circle into the 2 μm FLP site of a plasmid and the entire construction was integrated into a chromosome. Upon induction of the FLP gene under the GAL1 promoter the 2 μm circle was excised from the chromosome and the free plasmid was amplified from one to more than 20 copies per cell (Volkert and Broach, cited above). Since this amplification was observed using the entire culture a large proportion of the cells should have amplified their 2 μm circle.

Since pRS11 contains the 2 μm ORI the plasmid should be able to establish itself in high copy number after excision especially because the uncut plasmid transforms yeast at high frequency and confers an unstable LEU+ phenotype. Therefore one should be able to select for the presence of the plasmid after excision. If plasmid excision (event 124, FIG. 10) were the major event reverting the his3 disruption one would expect similar frequencies of prototrophs after selection for HIS+ (all recombination events) and HIS+ LEU+ (plasmid excision). Both strains RSY6 and RSY11 gave the same frequency of HIS+ colonies of about $4\times10^{-4}$ so that the frequency of the recombination events was not altered by the presence of the 2 μm ORI or the FLP site within the insert.

On −LEU −HIS selection medium again the same frequency of revertants were obtained for both strains RSY6 and RSY11 but this time the frequency was only $2\times10^{-6}$. To determine whether the LEU2 marker in HIS+ LEU+ isolates was carried on a freely replicating plasmid the isolates were tested for the stability of their LEU+ phenotype. Prototrophies carried on 2 μm based plasmids are lost from cells at about 1% per generation (see Broach et al. "Transformation in yeast: Development of a hybrid cloning vector and isolation of the CAN1 gene." Gene 8:121–133, 1979). Ten HIS+ LEU+ isolates from strain RSY6 as well as RSY11 were examined for the stability of their LEU+ marker after ten generations under nonselective conditions. Strain RSY6 only gave rise to colonies showing a stable LEU+ phenotype. Isolates from strain RSY11 yielded four colonies with an unstable LEU+ phenotype. As further test for the presence of a free excised plasmid, DNA was isolated from all 20 HIS+ LEU+ isolates and *E. coli* was transformed according to standard procedures as found in the publication of Sherman et al. entitled "Methods in yeast genetics, a laboratory manual," Cold Spring Harbor Laboratory. Cold Spring Harbor, N.Y., (1986) and in a publication by Maniatis et al. entitled "Molecular cloning, a laboratory manual." Cold Spring Harbor Laboratory Press, Cold Spring Harbor, N.Y. (1982). *E. coli* transformants were obtained only from the DNA of the four colonies showing an unstable LEU+ phenotype. A restriction digest as carried out according to methods described in the aforementioned Maniatis et al. publication shows that plasmids identical to pRS11 can be obtained as well as two larger plasmids as recombination products of the excised plasmid with both forms A and B of the yeast resident 2 μm plasmid. It is a salient feature of plasmids containing the FLP site to recombine with the 2 μm plasmid in yeast (see the review of Broach, 1981 cited above). It has been reported that integration of the 2 μm plasmid into yeast chromosomes leads to loss of the affected chromosome as well as a high frequency of recombination in a diploid. 2 μm circles contain the FLP gene which codes for a site-specific recombinase which accepts as substrate the FLP recombination target (FRT) site (see Broach et al. "Recombination within the yeast plasmid 2 μm circle is site specific." Cell 29:227–234, 1982). Since FLP promoted recombination might have an effect on our results with strain RSY11 the applicant mutated the FRT site of pRS11 before integration into the HIS3 locus to construct strain RSY11FRT−. This destroys the substrate for the FLP recombinase at the HIS3 locus. Without integration plasmid pRS11FRT− proved to transform yeast with high frequency and conferred an unstable LEU+ phenotype. This served as test for the replication ability of the plasmid. With strain RSY11FRT− a frequency of HIS+ leu− colonies similar to strains RSY6 or RSY11 was found. HIS+ LEU+ colonies arose on the average at a frequency of $5\times10^{-6}$, which is about two times more frequent than with strain RSY6 or RSY11 but still 100 times less frequent than the occurrence of HIS+ leu− colonies. This result indicates that plasmid excision is not the major recombination event involved in reversion of the gene disruption.

The liklihood that the plasmid might not be able to replicate after excision was reduced by the fact that plasmids pRS11 as well as pRS11FRT− both transformed yeast at high frequency and successful excision events were found bearing plasmids which do not differ in their stability to similar other 2 μm based plasmids. It has further been shown that the 2 μm plasmid could replicate in the majority of the cells after excision from the genome (see Volkert and Broach "Site specific recombination promotes plasmid amplification in yeast." Cell 46:541-550, 1986).

In summary plasmid excision could be demonstrated with strain RSY11 but it seemed to occur 100 times less frequently than reversion of the duplication deletion at HIS3. These results are rather independent of an active FRT site on the integrated plasmid and indicate that a mechanism different than plasmid excision (see FIG. 10) might be required to explain the majority of the reversion events. Since from the above experiments plasmid excision seemed to be unlikely to be the major mechanism for reversion of the duplication deletion other possible mechanisms were SCE (event 129) and/or SCC (event 128, FIG. 10). These two possibilities could be distinguished by determining whether the reciprocal product of the recombination event contains a single copy of the integrated plasmid (as for SCC, event 128, FIG. 10) or a duplication of the plasmid (as for SCE, event 126 FIG. 10). Since the cells containing the reciprocal products would be still his LEU+, they could not be selected for. Hence sectors adjacent to HIS+ recombinant sectors were examined by Southern blotting as described by Southern in a publication entitled "Detection of specific sequences among DNA fragments separated by gel electrophoresis." J. Mol. Biol. 98:503-517 (1975).

Colonies sectored for their HIS+ phenotype were isolated in six nonselective experiments using strain RSY6. The first four experiments were done with cells in stationary phase without irradiation and the last two experiments were done with log phase cells irradiated with 40 Joule/m² UV light giving about 40% survivors. The UV treatment caused about a three fold enhancement of the reversion rate. Nine colonies from spontaneously occurring events and 16 colonies from cells irradiated with 40 Joule/m² were used for Southern blotting. HIS— colonies were checked by Southern blotting (see a publication by Southern entitled "Detection of specific sequences among DNA fragments separated by gel electrophoresis." J. Mol. Biol. 98:503-517 (1975)) for the copy number of the integrated plasmid. Colonies containing a single integrated plasmid were used for recombination experiments and colonies containing a double integration event were used as controls for Southern blots testing for the reciprocal products after sister chromatid exchange. Entire colonies containing ½, ¼ or ⅛ HIS+ sectors were used. HIS+ sectors alone did not give any signal when probed with pBR322.

From the transformation of RS35/2-10C with pRS6 single as well as double integrants were obtained. In double integrants an additional fragment of about the size of the plasmid pRS6 (plasmid 116, FIG. 8) hybridized to pBR322. These colonies served as control for the detection of the duplication of the integrated plasmid after SCE (event 126, FIG. 10). After mixing DNA from a single integrant with ½, ¼ or ⅛ of DNA from a double integrant the band characteristic for the double integrant could still be easily identified. With the reasonable expectation that the cells containing the reciprocal product should encompass a sector of equal size to the ½, ¼ or ⅛ HIS+ sector our method should be valid for detection of a sector containing a duplication of the integrated plasmid. None of the 25 colonies examined gave any indication of a duplication suggesting that SCC might be the main mechanism responsible for reversion of the his3 disruption.

The genetic control of SCC (event 128, FIG. 10) has been determined using genes in all three DNA repair groups in yeast namely excision repair, postreplication repair and double strand break repair. These pathways are described in a publication by Cox and Game entitled "Repair Systems in Saccharomyces" Mutation Research 26:257-264 (1974). Until now only genes of the double strand break repair group have been positively identified to play a role in recombination. It has been found that RAD1, a gene involved in excision repair is involved in SCC. RAD1 is not involved in any other recombination mechanism in yeast, there being intrachromosomal heteroallelic conversion, interchromosomal crossing over and conversion (ICC) as well as meiotic conversion. Therefore the involvement of RAD1 in recombination has not previously been found in the previous art. Thus SCC is under different genetic control and therefore most likely is different in mechanism and this makes it also likely to show different inducibility than recombination events of the previous art. Because the recombination systems within the scope of this invention seem to be different in mechanism from the one operating in the recombination systems of the previous art the recombination systems within the scope of this invention is very valid because a type of DNA damage might be detectable which is different from the ones detected with the previous art systems. Hence it is important to note as explained in Example 2 that both SCC as well as the previous art system ICC are inducible with the mutagenic carcinogens methyl methanesulfonate, ethyl methanesulfonate as well as 4-nitroquinoline-N-oxide. On the other hand as explained in Example 3 the SCC system is much better inducible with the nonmutagenic carcinogens. The nonmutagenic carcinogens ethionine, safrole and urethane would not have been detected at all with the ICC system.

Interchromosomal conversion in diploids, the recombination system used in the previous art, has been shown to occur in $G_1$ as described in a paper by Fabre entitled "Induced intragenic recombination in yeast can occur during the $G_1$ mitotic phase." Nature 272:795-798 (1978) and is inducible in G1. In fact it has been shown that inducibility is up to 20 fold decreased in $G_2$ (see Fabre et al. "Gene conversion at different points in the mitotic cycle of *Saccharomyces cerevisiae*." Mol. Gen. Genet. 195:139-143, 1984).

The applicant has reproduced the method published in the aforementioned paper by Fabre et al. Mol. Gen. Genet. 195:139143 (1984) to obtain mostly $G_1$ (stationary) and $G_2$ arrested cells by using Methyl-Benzimidazole-Carbamate (MBC) to arrest the cells in $G_2$: Strain used for the experiment was RS112, the genotype of which is given below:

| MATa ura3-52 leu2-3,112 trp5-27 arg4-3 ade2-40 ilv1-92 HIS3::pRS6 LYS2 |
|---|
| MATα ura3-52 leu2Δ98 TRP5 ARG4 ade2-101 ILV his3Δ200 lys2-801 |

Media were the same as described at another part of the specification. Stationary cells were obtained by incubation of cells in liquid YPD at 30° C. for 48 hours. Stationary cells were more than 85% in G1. To obtain cells arrested in G2 the cells were incubated in YPD containing the fungicide methyl benzimidazol-2-yl carbamate (MBC) (stock solution 10 mg/ml) at a concentration of 100 μg/ml at a cell density of $10^7$ cells/ml for 5 to 7 hours at 30° C. Cells were checked microscopically for their phenotype until more than 90% showed the characteristic G2 arrest. Log phase cells were obtained by incubation of the cells in YEPD for the same time period without MBC. Log phase cultures contained cells in all stages. The cells were irradiated with UV light at a dose of 0–40 J/m2 and cells were held at G1, log or G2 for another two hours to allow repair of the damage in the respective stage. The cells were than collected by centrifugation and washed twice, plated for survivals onto SC medium, for determination of interchromosomal conversion events onto SC-Ade and for determination of SCC onto SC-His. MBC treatment never decreased the plating efficiency.

It has to be noted that log cells constitute a mixture of cells in all phases. Results for conversion between heteroalleles and between sister chromatids using the diploid strain RS112 are shown in Tables 1 and 2.

TABLE 1

| UV dose in J/m² | SCC in G1 | SCC in G2 | SCC in log phase |
|---|---|---|---|
| 0 | 4.4 | 4.7 | 4.3 |
| 10 | 7.5 | 5.1 | 15.8 |
| 20 | 7.6 | 4.0 | 26.1 |
| 30 | 9.1 | 5.4 | 31.3 |
| 40 | 9.9 | 5.1 | 44.2 |

In Table 1 values for SCC (sister chromatid conversion) are given in events per $10^4$ cells. The UV dose is given in Joule per square meter. The data show that, SCC is inducible by irradiation with the mutagenic carcinogen UV light; secondly the data show that SCC is only efficiently inducible when cells are growing in logarithmic culture.

TABLE 2

| UV dose in J/m² | ICC in G1 | ICC in G2 | ICC in log phase |
|---|---|---|---|
| 0 | 0.20 | 0.17 | 0.2 |
| 10 | 0.75 | 0.18 | 5.2 |
| 20 | 6.80 | 0.32 | 9.9 |
| 30 | 11.8 | 0.32 | 16.0 |
| 40 | 19.1 | 0.48 | 41.0 |

In Table 2 values given for ICC (interchromosomal conversion) the recombination system used in the previous art, are given in events per $10^5$ cells. The data show that ICC is not inducible in G2 but is well inducible in G1. The inducibility in S (logarithmically grown cells) cannot be allocated to the S (DNA synthesis) phase since log phase cells contain cells in all stages so that the inducibility could come about by inducibility of the cells in the log phase which are in G1 stage.

As previously reported the inducibility of interchromosomal conversion is reduced or abolished in G2. In the same strain and the same experiment sister chromatid conversion (SCC) is neither inducible in G1 nor in G2 but there was good inducibility in log phase cells. Since cells are not inducible for SCC in G1 or G2 phases the only phase which is left for possible induction in log cells is the S phase. Thus the system used as one of the preferred embodiments can detect DNA damage mainly in the S phase, monitoring agents which interfere with DNA replication and is in this respect again different from the previous art recombination system of heteroallelic conversion.

It is concluded that the preferred system selecting for genome rearrangements (SCC events) is sensitive to detect DNA damage which is induced during the S phase of the cell cycle. Therefore it is preferred that conditions are used in which a majority of the cells are in the S phase of the cell cycle. For instance the use of mutations, which at the restrictive temperature stop growth of the cells in the S phase. Thus, for example, the mutions cdc8 or cdc17 stop growth in the S phase at the restrictive temperature and might be used to synchronize the cells before exposure to the agents to be tested. SCC is likely to be inducible by all carcinogens acting during DNA synthesis. Such carcinogens, if the genetic damage they induce would be repaired by SSC would not be detected by any other system because conversion between sister chromatids does not cause mutations and is genetically silent unless a system specific for this genetic endpoint is used. Thus it is known that cancer is more likely to originate in proliferating tissue and growth of cells such as wound healing can result in cancer at a higher incidence than when there would be no cell growth. Thus it is likely that certain carcinogens deposited in the body act only during cell growth and thereby giving rise to the higher incidence of carcinogenesis when the tissue is growing. Thus it might be likely that the preferred embodiment screening for sister chromatid conversion is sensitive to detect those carcinogens which act only during cell growth and which are not detected by the previous art systems screening for mutations or heteroallelic conversion.

For predictive carcinogenesis it might be most advantageous to use yeast strains such as RS112 which incorporate as genetic endpoints systems selecting for SCC one of the preferred embodiments of this invention, heteroallelic conversion, a genetic endpoint of the previous art, crossing over between homologs, another genetic endpoint of the previous art, as well as mutation yet another genetic endpoint of the previous art. The different systems differ from each other in sensitivity to detect certain kinds of carcinogens and could together detect most if not all carcinogens. One of their best advantage if incorporated in one strain is also that the tests are more easy to carry out than the previous art "Ames Assay" which calls for five different Salmonella strains (see a publication by Ames at al. entitled "Methods for detecting carcinogens and mutagens with the Salmonella/mammalian-microsome mutagenicity test" published in Mutation Research 31:347–364, 1975). In addition yeast contains cytochrome P450 and for various agents which require metabolic activation in Salmonella no metabolic activation is needed in yeast (see a publication by Zimmermann et al. entitled "Testing of chemicals for genetic activity with *Saccharomyces cerevisiae*: a report of the U.S. Environmental Protection Agency Gene-Tox Program" published in Mutation Research 133:199–244, 1984). Thus it seems important that the preferred embodiment selecting for reversion of a disrupted gene is incorporated into any test battery assessing the potential hazard of an agent.

EXAMPLES

The following examples are presented to illustrate the preferred embodiments of this invention but are not to be deemed limitative thereof. Unless otherwise stated, all parts are by weight and all temperatures are in degrees centigrade.

The examples 1–3 relate to the most preferred embodiment of this invention, which is illustrated in FIG.

1 as construct 10 and whose construction is described in detail in the specification. Example 1 describes the construction of construct 10 in further detail. Examples 2 and 3 illustrates the use of this construct and Example 4 describes the construction of alternative preferred embodiments. Many of the procedures for constructing and/or characterizing construct 10 are well known to those skilled in the art. These prior art procedures are illustrated in the Examples by reference to prior art publications, each of which is hereby incorporated into this specification.

EXAMPLE 1: CONSTRUCTION OF THE RECOMBINATION SYSTEM

A strain containing the recombination system was deposited as "Saccharomyces cerevisiae RSY6" on Nov. 30, 1987, number 20871, with the American Type Culture Collection of Rockville, Md. by GeneBioMed, Inc.

A yeast strain with marker leu2— was used. The particular yeast strain used by the applicant was S35/2-10C, which had the following genotype: MATa, ura3—52, leu2—3,112, trp5—27, arg4—3, ade2—40, and ilv1—92; it was constructed by the applicant in accordance with the procedure described in Sherman et al. "Methods in yeast genetics" Cold Spring Harbor Laboratory Press, CSH, New York. Yeast strains RSY6, RSY11 and RSY11FRT— have plasmids pRS6, pRS11 and pRS11FRT— (FIG. 1) respectively integrated into the HIS3 gene of strain S35/2-10C thus disrupting the HIS3 gene.

pRS6 was constructed as follows: Plasmid pSZ515 plasmid 104 of FIG. 7 was obtained from Jack Szostak of the Department of Molecular Biology, Massachusetts General Hospital, Boston, Mass.; see the aforementioned publication by Orr-Weaver et al. Methods Enzymol. 101:228-245 (1983) This plasmid was cut with BamHI (for description see pages 14 and 15 of this specification, restriction enzymes were purchased from Bethesda Research Laboratory of Gaithersburg, Md.) and used according to the manufacturers recommendation and the HIS3 fragment (fragment 90 of FIG. 6) was separated from the rest of the plasmid by agarose gel electrophoresis in a commercially available gel tank obtained from Bethesda Research Laboratories of Gaithersburg, Md. A gel was prepared with 0.7% agarose (ultra pure, from Sigma Chemical Company of St. Louis, Mo. 63178) in TBE buffer containing per liter of distilled water 10.8 gram Tris (hydroxymethyl) aminomethane (hereinafter called Tris-base), 5.5 gram boric acid and 0.93 gram disodium ethylene diamine tetraacetate dihydrate (hereinafter called EDTA). The agarose was boiled in TBE buffer until dissolved and after cooling to 45° C. poured into the gel tank. the solidified gel was submerged into TBE buffer and the gel was electrophoresed with a commercially available power supply (from Bethesda Research Laboratories) at 30 volts for 12 hours. The DNA was made visible under UV light by staining with 0.5 microgram per milliliter ($\mu$g/ml) ethidium bromide and the desired band was located. The DNA fragment was isolated according to a publication by Dretzten et al. entitled "A reliable method for the recovery of DNA fragments from agarose and acrylamide gels" as appeared in Analytical Biochemistry 112 on pages 295 to 298 (1981). After making an incision with a scalpel in front of the band a piece of Wattman DE81 DEAE-cellulose paper (obtained from Fisher Scientific of Pittsburgh, PA) was inserted. The band was allowed to enter the DEAE paper by further electrophoresis in the same direction, and thereafter the paper was removed from the gel. The paper was placed into a 0.4 ml Eppendorff tube, and a hole was made in the bottom of the tube, the tube was placed inside a 1.5 ml Eppendorff tube and spun for 15 seconds in a Fisher microfuge, 0.1 ml of elution buffer containing 0.2 molar sodium chloride, 50 millimolar Tris base with a pH of 7.6, one millimolar EDTA and 0.1% of sodium dodecyl sulfate (obtained from Sigma Chemical Corporation) was added, and the elution buffer collected by centrifugation. This was repeated twice, and the eluate was extracted once with an equal volume of phenol, once with a 1:1 mix of phenol chloroform and once with chloroform. The obtained solution was precipitated with twice the volume of ice cold ethanol for 30 minutes at $-20°$ C. Thereafter, the precipitate was washed with a 70% solution of ethanol, vacuum dried, and redissolved in 10 ml of double distilled water.

This fragment was further cut with Hpa II, and the large fragment containing most of the HIS3 gene with a deletion of the promoter of the gene (see for the structure of the gene Struhl and Davis "A physical, genetic and transcriptional map of the cloned his3 region of *Saccharomyces cerevisiae*." J. Mol. Biol. 136:309-332 (1980) was isolated as described above. Plasmid pBR322 (100 of FIG. 7) was cut with ClaI and BamHI and the large fragment (102 of FIG. 7) was isolated. This fragment was ligated with the HIS3 gene containing the promoter deletion (fragment 106) to produce pRS5 (plasmid 108 of FIG. 7). Ligation was carried out by adding 0.2 Weiss units of T4 DNA ligase (obtained from Boehringer Mannheim, Indianapolis, Ind.) and one tenth of the following ligation buffer: 0.5 molar Tris base with a pH of 7.4, 0.1 molar magnesium chloride, 0.1 molar dithiothreitol, 10 millimolar spermidine, 10 millimolar adenosine triphosphate, and one milligram per milliliter of bovine serum albumine. Ligation was performed overnight at 4° C.

*E coli* strain SF8 was transformed with the ligation mix. *E. coli* transformation was started with an overnight culture of strain SF8 in LB medium. It is believed that strain SF8 has the following genotype: hsdr—, hsdm—, recA1, supE44, lacz4, leuB6, proA2, and thi1. 5 ml of Luria Broth (LB) medium containing 10 grams of tryptone, 5 grams of yeast extract, (both ingredients obtained from Difco Laboratories of Detroit, MI) 5 grams of sodium chloride per liter of medium was inoculated with a single bacterial colony, incubated overnight at 37° C. in a New Brunswick incubator with vigorous shaking. 0.3 ml of this culture were inoculated into 30 ml of fresh LB medium and incubated under vigorous shaking at 37° C. until the culture reached an OD at 600 nanometers of 0.6. The culture was chilled by placing onto an ice water bath and thereafter the cells were collected by centrifugation at 6,000 rounds per minute (hereinafter called rpm) in a Sorvall centrifuge obtained from I. Sorvall Inc. Newton, Ct. for five minutes. In the ice water bath one milliliter of an ice cold solution of 50 millimolar calcium chloride was added to the cell pellet and mixed. Ten microliters (hereinafter abbreviated $\mu$l) of the ligation mix was added to 5 $\mu$l of a solution of one molar calcium chloride and 85 $\mu$l of buffer containing 10 millimolar of the aforementioned Tris-base and one millimolar EDTA adjusted to pH of 8.0 with hydrochloric acid (this buffer is hereinafter called Tris/EDTA pH8.0). 0.2 milliliter of cell suspension was added to the DNA solution in small cooled plastic tubes. The solution was mixed gently and left on ice for 30 minutes. Thereafter the suspension was heated to 45° Celsius (C) in a water bath for two minutes and then placed again into the ice bath to cool down. Three milliliter of LB medium was added and the tubes were incubated at 37° C. for two hours. Thereafter the cells were collected by centrifugation at 6,000 rpm for 5 minutes and the cell pellet suspended in 0.5 ml LB medium. 0.1 milliliter was plated onto each of LB plates containing and 100 micrograms (hereinafter abbreviated μg) per milliliter of Ampicillin (obtained from Sigma Chemical Company).

Ampicillin resistant colonies were isolated, and plasmid DNA was isolated from them as a modification of the boiling method as published by Holmes and Quigley in a publication entitled "A rapid boiling method for the preparation of bacterial plasmids." Anal. Biochem. 114:193-197 (1981). One milliliter of $E.$ $coli$ culture containing the plasmid of interest was grown overnight in LB medium containing ampicillin. The cells were transferred to a 1.5 ml Eppendorff tube and spun down in a microfuge. The cells were resuspended in 0.4 ml of STET buffer consisting of 1 molar Tris-base adjusted to pH7.5 with hydrochloric acid, 20% "TRITON X100" (purchased from Fisher Scientific Company, manufactured by Rhom and Haas), 50% sucrose and 0.5 molar EDTA. Further 40 μl of a solution containing 10 mg of lysozyme (purchased from the aforementioned Sigma Chemical Company) per milliliter of double glass distilled water was added and the solution mixed. The solution was further boiled for 50-60 seconds and immediately thereafter placed in an ice-waterbath for 1 minute. The solution was spun in a microfuge for 10 minutes at four degrees Celsius and thereafter the resulting pellet was removed with a sterile toothpick. Further 500 milliliter of cold (−20 degrees Celsius) isopropanol was added the content mixed by inverting the tube several times and the tube was thereafter left in the freezer (−20 degrees Celsius) for 10 minutes. The solution was furthermore spun for 3 minutes in the microfuge at four degrees Celsius and afterwards the supernatant discarded; the pellet was resuspended in 50 μl of a Tris/EDTA buffer adjusted to pH8.0 with hydrochloric acid and 50 μl of a solution consisting of 5 molar lithiumchloride and 50 millimolar Tris/EDTA pH8.0 was added. The content of the tube was furthermore mixed and incubated in an ice-waterbath for 5 minutes. Thereafter the content was spun in a microfuge for 5 minutes at 4 degrees Celsius and the supernatant was removed and placed into a new Eppendorff tube. Furthermore 200 μl of cold ethanol (−20 degrees Celsius) was added, and after mixing of the content by inverting the tube several times the tube was left at −20 degrees Celsius for 10 minutes. After spinning of the tube for 3 minutes at 4 degrees Celsius, the precipitate was washed with one half milliliter of 80% ethanol. After another spin for 3 minutes in the microfuge at 4 degrees Celsius, the precipitate was dried in a desiccator by means of creating a vacuum with a waterpump for several minutes until the precipitate was dry. Thereafter the precipitate was dissolved in 60 μl of double glass distilled water or Tris/EDTA pH8.0 depending on the further procedure. The resulting solution contained about 2 microgram of plasmid DNA which was cut with restriction enzymes to determine which of the colonies contained the correct plasmid pRS5.

Plasmid pRS5 (108) was cut with KpnI and SalI to produce a second deletion at the 3' end of the HIS3 gene (plasmid 110 of FIG. 8). Plasmid YEp13 (112) obtained from H. Ruis, Department of Biochemistry, University of Vienna (constructed by Broach et al. and described in the aforementioned paper Gene 8:121-133 [1979]) was digested with SalI and partially with KpnI—the partial containing the entire LEU2 gene was isolated and ligated with the above isolated fragment of pRS5 (110) to yield pRS6 (116 of FIG. 8).

Plasmid pRS6 was isolated large scale from $E.$ $coli:$ 5 milliliter of LB medium with ampicillin was inoculated with a single bacterial colony, incubated overnight at 37° C. in a New Brunswick incubator with vigorous shaking. 2.5 milliliter of the overnight culture was inoculated into a two liter flask containing 500 milliliter of M9aa minimal medium: M9aa medium contained per liter of distilled water solution, 6 gram of sodium phosphate ($Na_2HPO_4$), 3 gram of potassium phosphate ($KH_2PO_4$), 0.5 gram of sodium chloride (NaCl), one gram of ammonium chloride ($NH_4Cl$), and 4 gram casaminoacids (obtained from Difco Laboratories). The medium was adjusted to a pH of 7.4 sterilized by autoclaving and after cooling the following solutions were sterilized by filtration and added, two milliliter of one molar magnesium sulphate ($MgSO_4$), 10 milliliter of 20% glucose, 100 μl one molar calcium chloride ($CaCl_2$) and one milliliter of 100 μg/ml of Ampicillin. The culture was vigorously shaken at 37° C. until it reached an optical density (OD) at 600 nanometer of 0.6 and 65 milligram of chloramphenicol (purchased from Sigma Chemical Comp.) were added and the culture was further incubated for another 14 hours in the same way. The cells were seperated by centrifugation in a GSA rotor for 10 minutes at 5000 rpm in a Sorvall centrifuge. Thereafter the cells from one liter initial culture were resuspended in 100 ml TS buffer containing 10% sucrose and 0.05 mol Tris-base adjusted to a pH of 8.0 with hydrochloric acid. The cell were again collected by centrifugation as described above and were chilled at 0° C. in an ice-water bath and resuspended in 10 ml ice cold TS buffer and transfered to a 50 ml flask. Two milliliter of a solution of 5 milligram per milliliter of freshly dissolved lysozyme (obtained from Sigma Chemical Comp.) was added, and the solution was mixed gently on ice for 10 minutes, four milliliters of a solution of ice cold 0.25 molar EDTA was added gently from the bottom of the flask and the mix left on ice for five minutes. 15 milliliter of triton lysis buffer consisting of a solution in distilled water of 10% "TRITON X-100", 0.05 molar Tris base adjusted to a pH of 8.0 with hydrochloric acid, and 0.05 molar EDTA were added and the solution was left for 10 minutes on ice. Thereafter the solution was spun in a SS34 rotor in a Sorvall centrifuge with 18,000 rpm at 4° C. for 60 minutes. The supernatant was collected and an equal volume of phenol, equilibrated with TE buffer, consisting of a solution in distilled water of 10 millimolar Tris base adjusted to a pH of 8.0 with hydrochloric acid and 1 millimolar EDTA, and an equal amount of chloroform was added. The solution was shaken for 3 minutes at room temperature and thereafter spun at 5,000 rpm in a SS34 rotor in a Sorvall centrifuge for 10 minutes and the supernatent was collected. The same procedure starting with the addition of phenol was repeated a second time and the water phases were joined and 17.5 milligram of sodium chloride was added per milliliter of solution. Absolute ethanol was added at wice the volume of the solution, the solution was gently mixed and left for 30 minutes in a freezer at −20° C. The solution was spun at 5,000 rpm for 5 minutes and thereafter the pellet containing the DNA was washed with 80% in distilled water of ethanol. The pellet was dried in an desiccator and was then dissolved in 5 milliliter TE buffer.

Another purification step using cesium chloride gradient centrifugation was added. To the TE solution 0.75 milliliter of a buffer consisting of one molar Tris base adjusted to a pH of 7.5 with hydrochloric acid and 0.1 milliliter of 0.5 molar EDTA in distilled water was added. 0.978 gram of cesium chloride per (weight of solution in gram plus 1.2) was added and the volume split in half and added each into a nitrocellulose centrifuge tube of a 50 Ti rotor, and 0.6 milliliter of 5 mg/ml of ethidium bromide was added to each and the solution topped up with paraffin, and the tubes were sealed. The tubes were mixed well and spun in a Beckman ultracentrifuge for 40 hours at 40,000 rpm at 20° C. The plasmid band was located using UV light and was removed with a syringe and transfered to a 30 ml centrifuge tube. The ethidium bromide was extracted five times with an equal volume of butan-1-ol which was saturated with TE buffer. The DNA was precipitated with three volumes of 70% ethanol in distilled water at $-20°$ C. for one hour and collected by centrifugation at 10,000 rpm for 15 minutes in a SS34 rotor in a Sorvall centrifuge and dissolved in 0.5 ml TE buffer. The DNA solution was dialysed against TE buffer for 20 hours with changes of the buffer. The OD at 260 nanometer of the solution was determined and the concentration of DNA calculated. The yield was about 700 µg of plasmid DNA.

To produce the HIS3 gene disruption plasmid pRS6 was cut with HindIII to produce a gap within the internal fragment of HIS3. Strain S35/2-10C. was transformed with the gapped plasmid according to the aforementioned description in Orr-Weaver et al. Methods Enzymol. 101:228-245 (1983) to give raise to strains RSY6. Transformation of yeast was carried out by treating intact cells with lithium acetate as described by Ito et al. in a publication entitled "Transformation of intact yeast cells treated with alkali cations." J. Bacteriol. 153:163-168 (1983). 300 milliliter of a culture of strain S35-2/10C in YEPD medium were grown overnight to 5 to $7 \times 10^6$ cells per milliliter from a fresh overnight culture. Cells were collected by centrifugation at 5,000 rpm for 5 minutes in a GSA rotor in a Sorvall centrifuge. The cells were resuspended in 1.5 ml of a solution of Tris/EDTA, pH 7.5 and 0.1 molar lithium acetat (obtained from Sigma Chemical company) and incubated for one hour at 30° C. with constant agitation. Five micrograms of the digested plasmid pRS6 was mixed with 40 µg of sonicated salmon sperm carrier DNA (obtained from Sigma Chemical Company) dissolved in Tris/EDTA buffer, sonicated with a MSE 150 Watt Ultrasonic Disintegrator (obtained from Measuring and Scientific Equipment Ltd. Manor Royal, Crawley, Great Britain) for 10 minutes, extracted once with an equal volume of phenol, precipitated with twice the volume ethanol, dried under vacuum produced by a water pump and redissolved in Tris/EDTA buffer in an Eppendorff tube and 0.2 ml of the cell suspension was added to the DNA. The suspension was incubated for 30 minutes at 30° C. with agitation in a New Brunswick controlled environment shaker. Thereafter 1.2 ml of a solution containing 40% polyethylene glycol 4000 (obtained from Sigma Chemical Company), TE buffer with a pH of 7.5, and 0.1 molar lithium acetate were added and the solution was gently mixed. The solution was incubated for another 30 minutes at 30° C. with agitation and thereafter heated for 7 minutes in a 42° C. waterbath. The cells were then collected by centrifugation in a Fisher microfuge for 5 seconds, washed twice with TE buffer with a pH of 7.5 and finally resuspended in one milliliter of TE buffer. 0.2 ml of this cell suspension was plated onto one Petri dish containing medium lacking leucine. Yeast media are described on page 20 of this specification.

Single LEU+ colonies were isolated and checked for their histidine phenotype. Histidine requiring colonies were checked by Southern blotting for the copy number and the presence of the integrated plasmid. A rapid procedure for preparation of small amounts of high molecular weight yeast DNA was used for screening large numbers of yeast colonies as described in a publication by Ciriacy and Williamson entitled "Analysis of mutants affecting Ty-mediated gene expression in *Saccharomyces cerevisiae*" which appeared in Mol. Gen. Genet. 182 on pages 159 to 163 (1981). Five milliliters of YPD medium was inoculated with a single colony of yeast and grown overnight to stationary phase. Cells were transfered to 15 ml sterile plastic centrifuge tubes and the cells were collected by centrifugation in a table top clinical centrifuge. Cells were resuspended in one milliliter of distilled water and transferred to an Eppendorf microfuge tube. The cells were resuspended in 0.4 ml of spheroblasting buffer containing 5 ml of SCE (one molar sorbitol, 0.1 molar sodium citrate, 6 millimolar EDTA with a pH of 7.0), 5 mg of zymolyase 5,000 (produced by Kirin brewery of Japan) and 40 µl of mercaptoethanol and incubated in this buffer for one hour at 37° C. Thereafter 0.4 ml of a solution containing 2% sodium dodecyl sulfate in 50 millimolar Tris base with a pH of 8.0 and 10 millimolar EDTA were added, and the tube was mixed gently until the solution cleared. 0.2 ml of 5 molar sodium chloride, was added and the solutions were mixed by inverting the tube. The mix was left one hour at 0° C. to precipitate the DNA. The DNA was collected by centrifugation in a Fisher microfuge (obtained from Fisher Scientific) for ten minutes and the supernatant was discarded. 0.4 ml of TE buffer with a pH of 7.5 was added and the DNA dissolved. Thereafter 0.4 ml of a mix consisting of phenol, chloroform and isoamylalcohol at a ratio volume per volume of 50:50:1 was added and the solutions mixed. The solutions were spun in a Fisher microfuge for 4 minutes and the supernatant was transferred into a new Eppendorff tube. 0.8 ml of absolute ethanol was added, the content was mixed, and the mix was left in the freezer for 30 minutes. The precipitated DNA was collected by centrifugation for 5 minutes in a Fisher microfuge, and the supernatant was discarded. The precipitate was dried in a vacuum and dissolved in 50 microliter of TE buffer. The ethanol precipitation was repeated once, and about 10 microliter was used per restriction enzyme digest.

The DNA was digested with the restriction enzyme PstI for two hours at 37° C. and loaded onto an agarose gel, and electrophoresis was performed at 30 volts overnight. The DNA was transferred to Gene Screen Membrane (purchased from New England Nuclear of 549 Albany Street, Boston, MA 02118) as indicated by the supplier for the Southern blotting procedure.

pBR322 DNA was radioactive labelled according to a procedure published by Feinberg and Vogelstein in a publication entitled "A technique for radiolabelling DNA restriction endonuclease fragments to high specific activity." Anal. Biochem. 132:6–13 (1983). The plasmid was linearized by digestion with PstI, and the solution was boiled for 7 minutes. The reaction was carried out at room temperature by adding the following reagents in the stated order: distilled water to a total of 50 μl, 10 μl of oligo-labelling buffer containing solutions A, B and C in a ratio of 100:250:150. Solution A contained one milliliter of solution O (containing 1.25 molar Tris Buffer adjusted to a pH of 8.0 with hydrochloric acid, 0.125 molar magnesium chloride), 18 microliter of 2-mercaptoethanol, 5 μl of desoxy adenosine triphosphate, 5 μl of desoxy thymidine triphosphate, 5 μl of desoxy guanosine triphosphate (each triphosphate at a concentration of 0.1 molar was previously dissolved in TE buffer (3 millimolar Tris base, 0.2 millimolar EDTA, adjusted to a pH of 7.0 with hydrochloric acid). Solution B contained 2 molar 4-(2-hydroxyethyl)-1-piperazineethanesulfonic acid (Hepes) titrated to a pH of 6.6 with 4 molar sodium hydroxide. Solution C contained 90 optical density units per milliliter hexadeoxyribonucleotides (obtained from P-L biochemicals, Milwaukee, Wis.), 2 μl of a solution of 10 mg per milliliter of bovine serum albumine (obtained from Bethesda Research Laboratories of Gaithersburg, Md.), the above prepared DNA, 5 μl of [$^{32}$P]dCTP at a specific activity of 3000–4000 curie per millimol and 10 microcurie per microliter (obtained from Amersham Coporation of Arlington Heights, Ill.), 2 units of the large fragment of *Escherichia coli* DNA polimerase I (obtained from Bethesda Research Laboratory). The mixture was incubated for 2.5 hours and the reaction was stopped by addition of 0.2 ml of a solution consisting of 20 milimolar sodium chloride, 20 millimolar Tris base adjusted to a pH of 7.5 with hydrochloric acid, 2 millimolar EDTA, 0.25% sodium dodecyl sulfate, one micromolar deoxycytidine triphosphate. The labelled DNA was used for Southern hybridization as described by Williamson, et al. in a publication entitled "Transposable elements associated with constitutive expression of yeast alcohol dehydrogenase II" published in Cell 23:605–614 (1981). A prehybridization mix was prepared with 3 ml of distilled water 0.6 milliliter of filtered 10% sodium sarcosylate and 0.6 milliliter of one milligram per milliliter of sonicated salmon sperm DNA. The hybridization mix was prepared in the same way except that the labelled DNA was added and both mixes were heated to 85° C. for 5 minutes in a water bath and thereafter cooled to 0° C. in a ice water bath for 5 minutes. In a heat sealable plastic bag (Sears' Seal-n-Save) the prehybridization mix was added to the NEN Gene Screen membrane and after the membrane has been moistened avoiding any air bubbles, the prehybridization mix was discarded. The hybridization mix was added and the bag was sealed and incubated over night at 65° C. The next day the bag was opened and the filter washed for 30 minutes in 500 ml of a solution per liter of distilled water of 11.69 gram of sodium chloride, 16.09 gram of sodium phosphate (Na$_2$HPO$_4$×7H$_2$O), 0.37 gram of EDTA and 1% sodium dodecyl sulfate prewarmed to 45° C. The filter was washed in the same way for another 30 minutes in a solution per liter of distilled water of 11.69 gram of sodium chloride, 16.09 gram of sodium phosphate (Na$_2$HPO$_4$.7H$_2$O), and 0.37 gram of EDTA. Thereafter the filter was washed for 45 minutes in the same way in a solution per liter of distilled water of 2.34 gram of sodium chloride, 3.22 gram of sodium phosphate (Na$_2$HPO$_4$.7H$_2$O), and 0.074 gram of EDTA. Thereafter the filter was dried at 85° C. for four hours and for autoradiography exposed to a Kodak X-O mat X-ray film. The integrated plasmid formed one band in case of a single integrant and two bands in case of a multiple integrant.

One colony showing a single copy integration event was used as strain RSY6 which was deposited at November 30 under "ATCC designation number 20871" with the American Type Culture Collection of 12301 Parklawn Drive, Rockville, Md. 20852.

A modification of a procedure published by Hirt "Selective extraction of polyoma DNA from infected mouse cell cultures." J. Mol. Biol. 26:365–369 (1967) was used for purification of plasmid DNA from yeast.

pRS11:Plasmid YEp13 (FIG. 9) was cut with HindIII, the restriction sites filled with Klenow polymerase according to standard methods (see e.g. the aforementioned book by Maniatis et al. "Molecular cloning: A laboratory manual" [1981]) and the blunt ends were ligated to yield pRS10 which lacks the HindIII site of YEp13. pRS10 was cut with KpnI and SalI and the fragment containing the 2 μm ARS; see for the location of the ARS in the 2 μm circle Broach and Hicks "Replication and recombination functions associated with the yeast plasmid, 2 μm circle." Cell 21:501–508 (1980) was isolated. Plasmid pRS6 was cut with SalI and partially with KpnI and the large partial containing the entire LEU2 gene was isolated and ligated with the pRS10 fragment containing the ARS.

pRS11FRT−: To construct plasmid pRS11 lacking the FLP recombination target site (Broach et al. "Recombination within the yeast plasmid 2 μm circle is site specific." Cell 29:227–234 (1982). pRS11 was cut with XbaI, sticky ends filled with Klenow polymerase as mentioned above and religated. The final product was identified by its lack of the XbaI restriction site.

Plasmids pRS11 and pRS11FRT− transformed yeast at high efficiency and DNA isolated from those transformants was used to retransform E coli demonstrating the free replicating nature of the plasmids.

EXAMPLE 2: TESTING OF MUTAGENIC CARCINOGENS

The strain used in this example was RS112 which was obtained by crossing strain RSY6 with strain 428. RSY6 contains the SCC system and was deposited at November 30 under "ATCC designation number 20871" with the American Type Culture Collection of 12301 Parklawn Drive, Rockville, Md. 20852. Strain 428 was obtained from M. Snyder, Department of Biology, at Yale University, New Haven, Conn. and was used because it contains the mutation his3Δ-200, the construction of which has been described in an article by Struhl entitled "Naturally occurring poly(dA-dT) sequences are upstream promoter elements of constitutive transcription in yeast, published in Proc. Natl. Acad. Sci. USA 82 on pages 8419–8423. Strains containing the his3Δ-200 mutation are readily available to those skilled in the art.

Strain RS112 has the following genotype:

| MATa ura3-52 leu2-3.112 trp5-27 arg4-3 ade2-40 ilv1-92 HIS3::pRS6 LYS2 |
|---|
| MATα ura3-52 leu2Δ98 TRP5 ARG4 ade2-101 ILV his3Δ200 lys2-801 |

Values for the intrachromosomal recombination system between deletion alleles of his3 are designated as SCC. Also strain RS112 contained heteroallelic mutations in ade2 so that the frequency of interchromosomal gene conversion (ICC) between heteroalleles in a diploid was determined. ICC was measured as recombination between the heteroalleles ade2-40 and ade2-101 by selecting for ADE+. Values obtained are given to compare the performance of the two systems.

The mutagenic carcinogens ethyl methanesulphonate (EMS), methyl methane sulphonate (MMS) and 4-nitroquinoline-N-oxide (NQO) were used as described on pages 18-23 of this specification and gave a strong induction for SCC (20-150 fold, see Table 3). References to the mutagenicity and carcinogenicity of these agents will be found in the aforementioned paper by McCann et al. "Detection of Carcinogens as Mutagens in the Salmonella/Microsome Test: Assay of 300 Chemicals, Proc. Nat. Acad. Sci. USA, vol. 72, No. 129 (1975), pp. 5135-5139 as well as in the publication series IARC International Agency for Research on Cancer: Monographs on the Evaluation of Carcinogenic Risk to Man Vol. 1-31, IARC Lyon, France (1973-1983), the disclosure of which is hereby incorporated by reference into this specification.

been tested for with the SCC system as described on pages 18-23 of this specification.

Formaldehyde causes nasal cancer in rats, see Ulsaner et al. published in the "Handbook of Carcinogen Testing, Milman H. A., E. K. Weisburger (ed) Noyes Publications, Park Ridge, N.J. pp 587-602 (1985) and Swenberg et al. in "Nongenotixic Mechanisms in Carcinogenesis" 25 Banbury Report, Cold Spring Harbor Laboratory, CSH, N.Y. pp151-158 (1987). The Handbook of Carcinogen Testing and the 25 Banbury Report are hereby incorporated by reference into this specification. Formaldehyde has been proposed to act as tumor promoter, see Trump and Berezesky at pages 69-84 of the aforementioned 25 Banbury Report. Formaldehyde produces a respectable increase in SCC of about 20 fold (see Table 4) and it also induces ICC.

Safrole produces liver cancer in mice and rats, see e.g., the aforementioned IARC Monographs and the aforementioned Handbook of Carcinogen Testing. As can be seen in Table 4 safrole gives a sizeable increase in SCC without a corresponding increase in ICC. Most interestingly, safrole is not only negative in the "Ames Assay", but is also negative in the rat liver foci assay,

TABLE 3

Mutagenic Carcinogens

| MMS | | | | EMS | | | |
|---|---|---|---|---|---|---|---|
| conc in % | survival in % | SCC/ $10^4$ cells | ICC/ $10^5$ cells | conc in % | survival in % | SCC/ $10^4$ cells | ICC/ $10^5$ cells |
| 0 | 100 | 0.97 | 0.45 | 0 | 100 | 0.97 | 0.45 |
| 0.001 | 100 | 3.9 | 1.9 | 0.02 | 98 | 4.1 | 1.3 |
| 0.005 | 97 | 11.4 | 14.4 | 0.1 | 91 | 18.1 | 15.8 |
| 0.01 | 87 | 46.6 | 42.3 | 0.2 | 37 | 25.3 | 28.9 |
| 0.02 | 35 | 129 | 62 | | | | |

| | | | | NQO | | | |
|---|---|---|---|---|---|---|---|
| | | | | conc in µg/ml | survival in % | SCC/ $10^4$ cells | ICC/ $10^5$ cells |
| | | | | 0 | 100 | 0.97 | 0.45 |
| | | | | 0.1 | 84 | 16.9 | 57.4 |
| | | | | 0.5 | 74 | 19.0 | 93 |
| | | | | 2 | 13.3 | 55.6 | 106 |

The mutagenic carcinogens are detectable with the SCC as well as with the ICC systems and in addition also with the "Ames Assay" and most other short term tests.

EXAMPLE 3: TESTING OF NONMUTAGENIC CARCINOGENS

The nonmutagenic carcinogens described below were chosen because they are negative with all 5 strains currently used in the "Ames Assay"; see the aforementioned McCann et al. paper. Also see Flora et al., "Genotoxic activity and potency of 135 compounds in the Ames reversion test and in a bacterial DNA-repair test." published in Mutation Research 133:161-198, 1984. Also see De Flora "Study of 106 organic and inorganic compounds in the Salmonella/microsome test." published in Carcinogenesis 2:283-298 (1981). Each of these agents has been shown to be an animal carcinogen. Strain RS112 which is used for this example has been described in Example 2. These agents have see Pereira at pages 152-178 of the aforementioned Handbook of Carcinogen Testing, and safrole is also negative in the SCE and chromosomal aberration assays with mammalian cells, see Morris et al. on pages 100-115 of the Handbook of Carcinogen Testing.

Ethionine is a liver carcinogen, see e.g. the aforementioned IARC monographs, it induces SCC at high doses without resulting in an increase of ICC (Table 4). Ethionine is also negative in the SCE and chromosomal aberration assays with mammalian cells see the aforementioned Morris et al. article.

Urethane is very effective in producing lung as well as skin tumors in mice, see the aforementioned IARC monographs and the aforementioned Handbook of Carcinogen Testing. Urethane induces SCC at high doses without an increase in ICC (Table 4).

Aminoantipyrine is a bladder carcinogen see e.g., Boyland et al. in a paper entitled "Further experiments on implantation of materials into the urinary bladder of mice" which appeared in the Br. J. Cancer 18 on pages 575-581. Aminoantipyrine induces SCC (Table 4).

TABLE 4

Nonmutagenic Carcinogens

| Formaldehyde | | | | Safrole | | | |
|---|---|---|---|---|---|---|---|
| conc in mg/ml | survival in % | SCC/ $10^4$ cells | ICC/ $10^5$ cells | conc in % | survival in % | SCC/ $10^4$ cells | ICC/ $10^5$ cells |

TABLE 4-continued

| Nonmutagenic Carcinogens | | | | | | | |
|---|---|---|---|---|---|---|---|
| 0 | 100 | 2.3 | 0.49 | 0 | 100 | 1.1 | 0.50 |
| 0.015 | 97 | 3.8 | 2.5 | 0.05 | 112 | 0.94 | 1.07 |
| 0.03 | 53 | 7.3 | 2.1 | 0.1 | 95 | 1.22 | 0.59 |
| 0.05 | 4.2 | 29.5 | 5.4 | 0.2 | 76 | 2.4 | 0.82 |
| 0.07 | 2.2 | 40.0 | 7.1 | 0.4 | 4.6 | 14.1 | 1.36 |

| Urethane | | | | Aminoantipyrine | | | |
|---|---|---|---|---|---|---|---|
| conc in mg/ml | survival in % | SCC/ $10^4$ cells | ICC/ $10^5$ cells | conc in mg/ml | survival in % | SCC/ $10^4$ cells | ICC/ $10^5$ cells |
| 0 | 100 | 0.97 | 0.45 | 0 | 100 | 1.17 | 0.50 |
| 10 | 107 | 1.9 | 0.66 | 10 | 97 | 1.02 | 0.75 |
| 20 | 51 | 4.8 | 0.40 | 20 | 73.3 | 1.80 | 1.8 |
| 40 | 10 | 5.3 | 0.78 | 40 | 0.89 | 25.8 | — |

| Ethionine | | | |
|---|---|---|---|
| conc in mg/ml | survival in % | SCC/ $10^4$ cells | ICC/ $10^5$ cells |
| 0 | 100 | 1.17 | 0.50 |
| 10 | 79 | 4.8 | 0.77 |
| 20 | 67 | 5.4 | 0.80 |

The frequencies for ICC are given in events per $10^5$ survivals, and the frequencies for SCC are given in events per $10^4$ survivals. It has to be noted that for sister chromatid recombination in mammalian cells the increase even with potent carcinogens is usually less than ten fold and also slight increases have been taken as positive results. For instance an increase in frequency of two fold has been taken to be significant; see a publication by Rudiger et al. entitled "Metabolites of diethylstilbestrol induce sister chromatid exchange in human cultured fibroblasts." published in Nature 281:392-394).

It seems to be one common feature of most nonmutagenic carcinogens that exposure often at toxicologically and pathologically significant doses is required to induce tumors, see Sivak et al. in the aforementioned Banbury Report. In comparison of the data presented in Table 3 for mutagenic carcinogens and Table 4 for nonmutagenic carcinogens the same seems to be true for SCC induction.

When the two recombination systems SCC and ICC are compared in their performance in detecting carcinogens it will be noticed that both systems are well inducible with the mutagenic carcinogens (Table 3). The nonmutagenic carcinogens on the other hand are in general much better inducible in the SCC system and at least the nonmutagenic carcinogens safrole, ethionine and urethane would not have been detectable with the ICC system.

For predictive carcinogenesis it might be most advantageous to use yeast strains such as RS112 which incorporate as genetic endpoints systems selecting for SCC one of the preferred embodiments of this invention, heteroallelic conversion, a genetic endpoint of the previous art, crossing over between homologs, another genetic endpoint of the previous art, as well as mutation yet another genetic endpoint of the previous art. The different systems differ from each other in sensitivity to detect certain kinds of carcinogens and could together detect most if not all carcinogens. One of their best advantage if incorporated in one strain is also that the tests are more easy to carry out than the previous art "Ames Assay" which calls for five different Salmonella strains (see a publication by Ames at al. entitled "Methods for detecting carcinogens and mutagens with the Salmonella/mammalian-microsome mutagenicity test" published in Mutation Research 31:347-364, 1975). In addition yeast contains cytochrome P450 and for various agents which require metabolic activation in Salmonella (incubation with the S9 supernatant), metabolic activation is not needed in yeast (see a publication by Zimmermann et al entitled "Testing of chemicals for genetic activity with Saccharomyces cerevisiae: a report of the U.S. Environmental Protection Agency Gene-Tox Program" published in Mutation Research 133:199-244, 1984). Thus it seems important that the preferred embodiment selecting for reversion of a disrupted gene is incorporated into any test battery assessing the potential hazard of an agent.

EXAMPLE 4: CONSTRUCTION OF ALTERNATE PREFERRED EMBODIMENTS

This example deals with the construction of alternative preferred embodiments and it is understood by those skilled in the art that many of the features and alleles used can be constructed in a different way without deviating from the scope of this invention. By way of illustration and not limitation the alleles mentioned in the specification can be used. The methods used are well known to those skilled in the art and most of them are described by Maniatis et al. in a publication entitled "Molecular cloning, a laboratory manual." Cold Spring Harbor Laboratory Press, CSH, NY (1982) and by Sherman et al. in a publication entitled "Methods in Yeast Genetics, a laboratory Manual," Cold Spring Harbor Laboratory Press, CSH, NY (1986).

One method for selection for genome rearrangement within the scope of this invention illustrated in FIG. 2 has been constructed by Alani et al. in a publication entitled "A method for gene disruption that allows repeated use of the URA3 selection in the construction of multiply disrupted yeast strains" published in Genetics 116:541–545 (1987), the disclosure of which is hereby incorporated by reference into this specification.

PNKY51 one of the plasmids used in this embodiment has been constructed as follows: The backbone, pNKY3 was made by deleting the $2\mu$ DNA from YEP24 (see Rose et al. "Structure and function of the yeast URA3 gene: expression in E. coli." Gene 29:113–124) with digestion with the restriction endonuclease EcoRI and by inserting a BglII linker at the remaining EcoRI site. This procedure regenerated the EcoRI site. A 1.1 kb BglII-BamHI fragment of pNKY294 (see Foster et al. "Genetic organization of transposon Tn10" Cell 23:201–213) bearing Salmonell hisG DNA (see Barnes "Cloning and restriction map of the first part of the histidine operon of *Salmonella typhimurium*." J. Bacteriol. 147:124–134, 1981) was inserted into the BGLII site of pNKY3 to form pNKY49. Further the same aforementioned 1.1 kb hisG fragment was inserted at the BamHI site of pNKY49 to form pNKY50. Thereafter the EcoRI site at the 5' end of URA3 was destroyed by fill-in and ligation reactions. The resulting plasmid pNKY51 contained a 3.8 kb hisG-URA3-hisG fragment that was gel isolated after digestion with BglII and BamHI.

PNKY1009 which can be directly used to transform yeast in order to construct one of the possible systems within the scope of this invention has been constructed as follows: The BamHI site in YRP7 (see the aforementioned paper by Sherman et al. entitled "Methods in yeast genetics") was destroyed by fill-in and ligation reactions and a BamHI linker was inserted into the EcoRV site to form pNKY1006. The 3.8 kb BglII-BamHI fragment of the aforementioned plasmid pNKY51 was inserted into the BamHI site within the TRP1 gene of pNKY1006 to form pNKY1009.

Plasmid pNKY1009 was digested with EcoRI and BglII and the 4.6 kb fragment gel purified. Yeast strain S35/2-10C (MATa; ura3-52; leu2-3,112; trp5-27; arg4-3; ade2-40; ilv1-92) was reverted for its trp5 marker and transformed with the 4.6 kb fragment to delete the TRP1 gene. The deletion was verified by the trp1− phenotype. This strain can be used to screen for the potential of an agent to induce genome rearrangement when in conjunction with medium containing 5-fluoroorotic acid as described in the specifications.

One other preferred embodiment within the scope of this invention has been constructed by Fasullo et al. in a publication entitled "Recombinational substrates designed to study recombination between unique and repetitive sequences in vivo" published in Proc. Natl. Acad. Sci. USA 84:6215–6219, (1987), the disclosure of which is hereby incorporated by reference into this specification.

The system is illustrated in FIG. 4 and has been be constructed as follows:

The plasmid YIp5 was used. Construction of this plasmid is described in Scherer et al. "Replacement of chromosome segments with altered DNA sequences constructed in vitro." Proc. Natl. Acad. Sci. USA 1979:4951–4955, (1979). YIp5 his3-Δ3' and his3-Δ5' was constructed by separately subcloning the 800 base pair BamHI-BglII his3 fragment and the 1.4 kb BamHI his3-Δ5' into YIp5. The his3-Δ5' allele was called his3-Δ2619 and has been published in an article by Struhl et al. published in J. Mol. Biol. 136:309–332 (1980). The yeast strains were constructed by transformation of the appropriate plasmids. All strains contained the his3Δ200 allele. Plasmids were targeted to homologous sites in the genome by restriction endonuclease digestion at the appropriate site in the plasmid.

Yet another preferred embodiment within the scope of this invention has been constructed by Fasullo et al. in the aforementioned paper published in Proc. Natl. Acad. Sci. USA 84:6215. This system is illustrated in FIG. 3 and has been constructed as follows:

The plasmid YIp5 his3-Δ(3'5') was constructed by subcloning a BamHI-KpnI fragment of his3Δ2639 (see the aforementioned publication Struhl et al. J. Mol. Biol. 136:309–332, 1980) into YIp5. Additional plasmids were constructed to integrate this plasmid into different regions of the genome. These plasmids were constructed by subcloning the appropriate EcoRI restriction fragments into these plasmids. Yeast strains harboring these plasmids integrated into the genome as well as the his3Δ200 allele can be used in this embodiment.

Yet another preferred embodiment within the scope of this invention comprises a naturally occurring duplication of genes and is illustrated in FIG. 5. The system utilizes the mating type of yeast which is described in a review by Herskowitz and Oshima in a publication entitled "Control of cell type in *Saccharomyces cerevisiae*. Mating type and mating type interconversion." In a book edited by J. N. Strathern et al. entitled "The Molecular Biology of the Yeast Saccharomyces," Cold Spring Harbor Laboratory press CSH, NY (1981). The preferred embodiment within the scope of this invention is called heterothallic mating type switching and has been developed by Schiestl and Wintersberger in a publication entitled "X-ray enhances mating type switching in heterothallic strains of *Saccharomyces cerevisiae*" published in Mol. Gen. Genet. 186:512–517 (1982), the disclosure of which is hereby incorporated by reference into this specification.

Haploid cells of the yeast Saccharomyces cerevisiae can be of mating type a or α. Cells of the opposite mating type can mate with each other to produce a/α diploids which can sporulate, but are unable to mate. The mating type is determined by the MAT locus on chromosome III. To show an a or α phenotype, expression of a or α information is required at MAT, whereas diploids are heterozygous for MAT and expression of both alleles is needed for sporulation (review: Herskowitz and Oshima In: The Molecular Biology of the Yeast Saccharomyces, Cold Spring Harbor Laboratory press CSH, NY, 1981). In addition two silent mating type loci are present on chromosome III, HMLα and HMRa respectively, left and right from MAT.

Haploid cells can switch from one mating type to the other by unidirectional intrachromosomal gene conversion, replacing the sequence at MAT by one from a silent locus Homothallic strains can interconvert their mating types as often as every cell division. They contain the HO gene and a site-specific endonuclease, YZendo, which cuts exclusively at the MAT locus and thus initiates switching. Heterothallic strains on the other hand, interconvert only about once per $10^6$ cells, contain the ho allele and lack any detectable YZendo activity.

Schiestl et al., published in the aforementioned paper Mol. Gen. Genet. 186:512–517 (1982), have developed a system to measure the frequency of heterothallic mating type switching. Cells in which the mating type was changed were trapped by mating to tester cells with complementing markers and the diploids were selected on a special medium. The procedure comprises the following steps:

A switching strain is used and may be any yeast strain with the mating type a as long as it has at least three complementing markers to the tester strain. The tester strain is a strain containing only MATa information at all three mating type loci, so that it cannot change its type. One of these tester strains is K123 (MATa mar1 cyh2 his4 leu2 thr4 ho HMLa HMRa) which was used in the aforementioned Schiestl et al. paper and which is readily available from the authors. Stationary phase cells from a freshly isolated haploid colony of the switching strain were sonicated with ultrasound. Thereafter the cells can be treated with the agents tested for their potential to induce genome rearrangements. Afterwards cells were incubated in liquid YEPD medium containing 1% yeast extract, 2% peptone, 2% dextrose and water until buds became visible. This was done to compensate for the growth retardation of treated cells versus untreated cells. The exact fraction of survivors was determined by plating cells on YEPD medium solidified with 2% agar. Stationary phase cells from the tester strain were sonicated and $4 \times 10^8$ cells per milliliter of distilled sterile water were mixed with about $2 \times 10^7$ surviving switching cells. Portions of 0.25 milliliter cell mixture were plated onto Petri dishes (diameter 10 centimeters) containing a medium containing enough complete medium so that cells of the switching strain after changing their mating type can mate with the tester cells but also with enough selective medium so that the prototrophic diploids which are formed during mating can grow on the medium after the medium was depleted of the growth factors required by the haploids. The medium to best fit this requirement was empirically determined and contained 0.05% yeast extract, 0.1% peptone, 2% dextrose, 0.67% yeast nitrogen base with ammonium sulfate and without amino acids and distilled water. All these media supplements were obtained from Difco Laboratories, Detroid, Mich. 48232. The colonies are countable after incubation at 30 degrees Celsius for 5-7 days.

An enhancement of the switching frequency has been detected by treating cells with DNA damaging agents (see Schiestl and Wintersberger in a publication entitled "Induction of mating type interconversion in a heterothallic strain of *Saccharomyces cerevisiae* by DNA damaging agents" Mol. Gen. Genet. 191:59–65, 1983).

In yet another preferred embodiment within the scope of this invention mammalian cells can be used and the genetic events shown in FIGS. 1 to FIG. 4 can be in an equivalent fashion constructed with mammalian cells. The selectable markers include the herpes simplex virus type 1 gene coding for thymidinekinase, H-TK, the neomycin (neo) gene of Tn5, which confers G418 resistance to transformed mammalian cells and the bacterial plasmid encoded hygromycin-B-phosphotransferase (hph) gene which confers resistance to hygromycin-B in mammalian cells and the like. For a description and a summary of the usefulness of these genes see the aforementioned book by R. Kucherlapati entitled "Gene Transfer". Plenum Press, N.Y.

The SCC system in mammalian cells can be constructed in three phases. First the plasmids required can be constructed, secondly the plasmids can be integrated into the genome of different cell lines, and then single copy integrants can be selected as determined by Southern blotting.

General Methods: *E. coli* strain HB101 (hsdr$^-$, hsdm$^-$, recA1, supE44, lacz4, leuB6, proA2, thi1) or other suitable *E. coli* strains can be used. Large scale as well as small scale plasmid isolation from *E. coli*, *E. coli* transformation and electrophoresis can be performed as described above. Isolation of DNA fragments from agarose gels can be carried out using the Geneclean kit from Bio 101, La Jolla, Calif., as recommended by the supplier.

The systems in mammalian cells can be constructed by replacing the genes LEU2, TRP1, URA3, LYS2, and the like of yeast with the aforementioned selectable dominant markers HTK, neo and hph of mammalian cells. The HTK system allows one to select positively for the TK$^+$ phenotype on medium supplemented with hypoxanthine, aminopterin and thymidine (HAT medium) and negatively for the TK$^-$ phenotype on medium supplemented with hypoxanthine and bromodeoxyuridine (HBu medium) so that it allows determination of recombination events by selection for the presence of the gene as in FIGS. 1, 3 and 4 as well as selection against the presence of the gene as in FIG. 2. The neo gene can be selected for on medium supplemented with G418 and the hph gene can be selected for on medium supplemented with hygromycin-B. The neo and the hph genes can be used for constructs analogous to FIGS. 1, 3 and 4.

Three plasmids can be constructed as follows: Plasmid A contains deletion alleles of the hph gene flanking the neo gene on pBR322 or another appropriate vector: From a plasmid containing the hph gene such as pLG61, described in a publication by Gritz and Davies published in a publication entitled "Plasmid-encoded hygromycin B resistance; The sequence of hygromycin B phosphotransferase gene" published in Gene 25:353–358 (1983) an EcoRI BglIII fragment can be subcloned containing most of the hph gene deleted for 279 basepairs at its 5' end. In addition a SacII SalI fragment containing most of the hph gene deleted for 243 basepairs at its 3' end can be separately subcloned. Each subclone has to be be tested to assure its hygromycin sensitive phenotype in *E. coli* as well as in mammalian cells. The final construct contains the Tn5 neo$^r$ gene on a HindIII fragment from plasmid pK0.neo (obtained from Douglas Hanahan of the Department of Biochemistry, at Harvard University, Cambridge, Mass.) flanked by the deletion alleles of the hph gene in the orientation: 5'hph $\Delta - 3'$, neo, $\Delta 5'$ hph3', pBR322 ($\Delta$=deletion). The two deletion alleles of the hph gene share 537 basepairs of homology which is more than sufficient in length to undergo homologous recombination, see e.g., Letsou and Liskay at pages 383 to 409 of the aforementioned book by Kucherlapati entitled "Gene Transfer". Plenum Press, N.Y. Plasmid A can be digested at a single site within pBR322 to transform mammalian cell lines.

Plasmid B can contain deletion alleles of the neo gene flanking the hph gene on pBR322 or another appropriate vector. From plasmid pK0.neo a 680 basepairs HindIII NaeI fragment containing most of the neo gene deleted for 162 basepairs of its 3' end can be subcloned. In addition a HindIII PvuII fragment containing the neo gene deleted for 234 basepairs of its 5' end can be subcloned. Each subclone has to be tested for its kanamycin sensitivity in *E. coli* and for its G418 sensitivity in mammalian cells. The final construct contains the hph gene flanked by the deletion alleles of the neo gene in the orientation: 5'neo$\Delta - 3'$, hph, $\Delta 5'$neo3', pBR322. The two deletion alleles of the neo gene share 396 basepairs of homology which is sufficient in length to undergo homologous recombination.

Plasmid C can be constructed and oriented like plasmid A with the BamH1 fragment from plasmid pTK2.0 (see a publication by Zipser et al. entitled "Mapping function domain in the promoter region of the herpes thymidin kinase gene" published in Proc. Natl. Acad. Sci. USA 78 on pages 6276 to 6280, 1981; kindly provided by Dr. Louise Chow of the Department of Biochemistry, School of Medicine University of Rochester, Rochester, N.Y.) containing the HTK1 gene instead of the HindIII fragment containing the neo gene.

As host cell lines for the recombination systems in plasmids A, B and C mammalian cell lines can be used. A variety of cell lines are accessible in the laboratory of Dr. George Abraham (Department of Immunology, Medical School, University of Rochester) and have been well characterized in his laboratory. Many of them can be usable for plasmids A and B, but prior to use they have to be tested for their sensitivity to the drugs G418 and hygromycin. For use of plasmid C it it is necessary to select TK⁻ mutants on HBu medium. As a parallel approach for use of plasmid C murine LTK⁻ cells can also be used.

After digestion of plasmids A–C within the pBR322 sequence the cell lines can be transformed using the $CaPO_4$ DNA mediated gene transfer, see Wigler et al., Proc. Natl. Acad. Sci. USA 76:1373–1376 (1979) and Corsaro and Pearson "Enhancing the efficiency of DNA-mediated gene transfer" published in Somatic Cell Genet. 7:603–616 (1981). As general medium to grow and select for tranformants Dulbecco modified Eagle medium supplemented with 10% fetal calf serum (both available from Gibco Laboratories, Grand Island, N.Y.) can be used and cell lines should be grown under an atmosphere of 5% $CO_2$. Selection for plasmid A can be carried out in the above medium supplemented with G418 sulfate (available from Gibco, Grand Island, N.Y.), selection for plasmid B can be carried out in the above medium supplemented with hygromycin-B (available from Eli Lilly and Company) and selection for plasmid C can be carried out in the above medium supplemented with hypoxanthine, aminopterin and thymidine (available from Gibco). Cell lines with single copy integrants should be selected according to Letsou and Liskay at pages 383 to 409 of the aforementioned book by Kucherlapati entitled "Gene Transfer". Plenum Press, N.Y. The basic method involves transformation of cell lines with a small amount of linearized plasmid (1–100 ng/$4 \times 10^4$ cells) in the presence of excess TK⁻carrier DNA (10–20 $\mu$g/$4 \times 10^4$ cells). This protocol has been determined to optimize the yield of single copy integrants. Candidates for single copy integrants are determined by Southern blotting according to a modification (see Example 1) of the procedure by Southern entitled "Detection of specific sequences among DNA fragments separated by gel electrophoresis." in J. Mol. Biol. 98:503–517 (1975). Genomic DNA can be isolated from single transformants and can be digested with an enzyme which has a single restriction site in the plasmid, either in the pBR322 sequence or in the nonhomologous parts of the two deletion alleles. After electrophoresis and transfer to nitrocellulose, the filters should be probed with radiolabelled purified fragments (see Example 1) of the selectable gene, which is the neo gene in construct A, the hph gene in construct B and the HTK1 gene in construct C. Single copy integrants will give only one band with at least two different restriction enzymes.

With the above mentioned procedure 1 to 3, single copy cell lines per 20 primary transformants should be obtained (see Letsou and Liskay at pages 383 to 409 of the aforementioned book by Kucherlapati entitled "Gene Transfer") which will be used to determine the rate of recombination. In case of construct A and construct C, selection for hygromycin-B resistance and in case of construct B selection for G418 resistance will be applied. In analogy to the data obtained with yeast (see Example 1) it is predicted that most recombinants have lost their resistance marker used in the primary selection for transformants; that is for instance in construct A cells should have converted from a G418 resistant, hygromycin-B sensitive phenotype to a hygromycin-B resistant, G418 sensitive phenotype. If this turns out to be true, the determination of the rate of recombination could be greatly simplified so that for instance in construct A in the culture of cells grown for the recombination test selection for G418 resistance is applied before the cells are treated with the test agents and recombinants are selected on medium supplemented with hygromycin-B. This selection scheme prevents accumulation of recombinants in the preculture and minimizes the fluctuation in the frequencies obtained. The use of this selection scheme in yeast is largely responsible for the detection of nonmutagenic carcinogens which show a less dramatic effect, for instance ethionine (see specification and Example 1).

As known to those skilled in the art, any other selectable markers in mammalian cells can be used instead of markers HTK, neo or hph, in conjunction with a specified medium selecting for the presence or against the presence of those markers to construct systems equivalent to the ones shown in FIGS. 1 to 4. The aforementioned systems are within the scope of this invention.

While the invention has been particularly shown and described with reference to certain preferred embodiments thereof, it will be understood by those skilled in the art that various changes in form and details may be made therein without departing from the spirit and scope of the invention.

I claim:

1. A process for screening an agent to determine its effect upon the frequency of deletions in Saccharomyces cerevisiae. comprising the steps of:
    (a) providing at least a first portion and a second portion of a viable strain of the unicellular yeast Saccharomyces cerevisiae comprising repeated genetic elements in its haploid genome, wherein:
        1. said repeated genetic elements are selected from the group consisting of functional and nonfunctional genetic elements, and
        2. said repeated genetic elements are sufficiently homologous so that, under ambient conditions, they recombine with each other and give rise to an identifiable deletion at the rate of at least about $1 \times 10^{-9}$ occurrences per cell per generation;
    (b) providing a growth medium which enables the identification of those Saccharomyces cerevisiae yeast cells which have undergone said deletion;
    (c) exposing at least said first portion of said viable strain of yeast to the agent to be tested, thereby producing an exposed strain of yeast;
    (d) preventing the exposure of said second portion of said viable strain of yeast to the agent to be tested, thereby producing an unexposed strain of yeast;
    (e) contacting said exposed strain of yeast with said growth medium;
    (f) contacting said unexposed strain of yeast with said growth medium;
    (g) incubating said exposed strain of yeast while it is in contact with said growth medium;
    (h) incubating said unexposed strain of yeast while it is in contact with said growth medium; and
    (i) determining the extent to which each of said exposed strain of yeast and said unexposed strain of yeast has undergone said deletion.

2. The process as recited in claim 1, wherein said repeated genetic elements are selected from the group consisting of nonfunctional genetic elements.

3. The process as recited in claim 2, wherein said strain of yeast is provided by disrupting a gene which is selectable for.

4. The process as recited in claim 3, wherein said repeated genetic elements flank a gene which is selectable for.

5. The process as recited in claim 4, wherein said repeated genetic elements are deletion alleles.

6. The process as recited in claim 5, wherein said deletion alleles are selected from the group consisting his3—, trpl—, leu2—, ura3—, and lys2—.

7. The process as recited in claim 4, wherein said gene which is selectable for is selected from the group consisting of LEU2, HIS3, TRP1, URA3, and LYS2.

8. The process as recited in claim 7, wherein said repeated genetic elements are deletion alleles.

9. The process as recited in claim 8, wherein said deletion alleles are selected from the group consisting of his3—, trpl1—, leu2—, ura3—, and lys2—.

10. The process as recited in claim 9, wherein said deletion alleles are his3—.

11. The process as recited in claim 10, wherein said gene which is selectable for is LEU2.

12. The process as recited in claim 1, wherein said strain of yeast corresponds to the yeast strain deposited under ATCC accession number 20871 on Nov. 30, 1987 as "*Saccharomyces cerevisiae*, RSY6."

13. The process as recited in claim 1, wherein said strain of yeast is provided by integration of a plasmid into its haploid genome.

14. The process as recited in claim 13, wherein said plasmid contains an internal fragment of a gene which, upon integration into the genome, provides said repeated genetic elements.

15. The process as recited in claim 14, wherein said plasmid contains an internal fragment of the HIS3 gene.

16. The process as recited in claim 4, wherein said gene which is selectable for is provided by integration of a plasmid.

17. The process as recited in claim 16, wherein said plasmid contains an internal fragment of a gene which, upon integration into the genome, provides said repeated genetic elements.

18. The process as recited in claim 16, wherein said gene which is selectable for is the LEU2 gene.

19. The process as recited in claim 18, wherein said plasmid corresponds to the plasmid deposited as ATCC designation number 67568 on Nov. 30, 1987.

20. The process as recited in claim 18, wherein said plasmid is contained *Escherichia coli.*

* * * * *